US011938128B2

(12) United States Patent
Gavathiotis et al.

(10) Patent No.: US 11,938,128 B2
(45) Date of Patent: Mar. 26, 2024

(54) SMALL MOLECULE BAX INHIBITORS AND USES THEREOF

(71) Applicants: Albert Einstein College of Medicine, Bronx, NY (US); The University of Manitoba, Winnipeg (CA)

(72) Inventors: Evripidis Gavathiotis, Roslyn, NY (US); Richard N. Kitsis, New York, NY (US); Thomas P. Garner, Long Island City, NY (US); Dulguun Amgalan, Bronx, NY (US); Lorrie Kirshenbaum, Winnipeg (CA); Felix Kopp, Brooklyn, NY (US)

(73) Assignees: Albert Einstein College of Medicine, Bronx, NY (US); The University of Manitoba, Winnipeg (CA)

( * ) Notice: Subject to any disclaimer, the term of this patent is extended or adjusted under 35 U.S.C. 154(b) by 0 days.

(21) Appl. No.: 16/492,300

(22) PCT Filed: Mar. 9, 2018

(86) PCT No.: PCT/US2018/021644
§ 371 (c)(1),
(2) Date: Sep. 9, 2019

(87) PCT Pub. No.: WO2018/165494
PCT Pub. Date: Sep. 13, 2018

(65) Prior Publication Data
US 2020/0009132 A1 Jan. 9, 2020

Related U.S. Application Data

(60) Provisional application No. 62/469,551, filed on Mar. 10, 2017.

(51) Int. Cl.
| | | |
|---|---|---|
| *A61K 31/496* | (2006.01) | |
| *A61K 31/495* | (2006.01) | |
| *C07D 209/86* | (2006.01) | |
| *C07D 209/88* | (2006.01) | |
| *C07D 279/26* | (2006.01) | |
| *C07D 295/13* | (2006.01) | |

(52) U.S. Cl.
CPC .......... *A61K 31/496* (2013.01); *A61K 31/495* (2013.01); *C07D 209/86* (2013.01); *C07D 209/88* (2013.01); *C07D 279/26* (2013.01); *C07D 295/13* (2013.01)

(58) Field of Classification Search
CPC ........................... A61K 31/495; A61K 31/496
See application file for complete search history.

(56) References Cited

U.S. PATENT DOCUMENTS

| | | | | |
|---|---|---|---|---|
| 3,928,341 A * | 12/1975 | Delarue | ............... | C07D 213/74 544/124 |
| 4,292,321 A * | 9/1981 | Pattison | ............... | C07D 211/52 514/278 |
| 8,053,436 B1 | 11/2011 | Halazy et al. | | |
| 2012/0040933 A1 | 2/2012 | Halazy et al. | | |
| 2015/0335671 A1* | 11/2015 | Gavathiotis | ........ | G01N 33/5008 514/25 |

FOREIGN PATENT DOCUMENTS

| | | | |
|---|---|---|---|
| JP | 2007223916 A * | 9/2007 | |
| WO | WO-2010033643 A2 * | 3/2010 | ............. A61K 31/47 |
| WO | 2017/008060 A1 | 1/2017 | |

OTHER PUBLICATIONS

Wise et al. Journal of Medicinal Chemistry (1985), 28(5), pp. 606-612 (Year: 1985).*
Chen et al. Tetrahedron, 2011, vol. 67, pp. 5883-5893 (Year: 2011).*
Cao et al. Bioorganic & Medicinal Chemistry Letters, 2008, vol. 18, pp. 5238-5241 (Year: 2008).*
Registry No. 765216-90-8 (Entered STN Oct. 18, 2004) (Year: 2004).*
Registry No. 499987-00-7 (Entered STN Mar. 19, 2003) (Year: 2003).*
Bourquin et al. Helvetica Chimica Acta., 1958, vol. 41, pp. 1072-1108 (Year: 1958).*
Ludwig et al. Journal of the American Chemical Society, 1954, vol. 76, pp. 2891-2893 (Year: 1954).*
Li et al. International Journal of Pharmaceutics, 2005, vol. 303, pp. 113-124 (Year: 2005).*
Gasiorowski et al. Cellular & Molecular Biology Letters, 2003, vol. 8, pp. 927-942 (Year: 2003).*
Registry No. 110151-58-1 (Entered STN Sept. 5, 1987) (Year: 1987).*
Registry No. 123937-31-5 (Entered STN Nov. 23, 1989) (Year: 1989).*

* cited by examiner

*Primary Examiner* — James D. Anderson
(74) *Attorney, Agent, or Firm* — Fox Rothschild LLP

(57) ABSTRACT

Compounds, compositions and method of using these compounds are disclosed for treating a disease or disorder in which it is desirable to inhibit BAX, such as a cardiovascular disease or disorder.

22 Claims, 26 Drawing Sheets

Specification includes a Sequence Listing.

SMALL MOLECULE BAX INHIBITORS AND USES THEREOF

CROSS-REFERENCE TO RELATED APPLICATIONS

This application claims the benefit of U.S. Provisional patent application No. 62/469,551, filed on Mar. 10, 2017, the contents of which is herein incorporated by reference in its entirety.

BACKGROUND OF THE INVENTION

Throughout this application various publications are referred to by number in parentheses. Full citations for these references may be found at the end of the specification. The disclosures of these publications, and all patents, patent application publications and books referred to herein, are hereby incorporated by reference in their entirety into the subject application to more fully describe the art to which the subject invention pertains.

Apoptosis is an evolutionarily conserved process that plays a critical role in embryonic development and tissue homeostasis. The dysregulation of apoptosis is pivotal to a number of high mortality human pathogenesis including cardiovascular diseases and neurodegenerative diseases. The pro-apoptotic Bcl-2-associated x-protein (BAX) induces mitochondrial outer-membrane permeabilization and represents a key gatekeeper and effector of mitochondrial apoptosis. In addition, BAX facilitates opening of the mitochondrial inner membrane permeability transition pore, thereby functioning as a pivotal activator of necrosis. Thus, inhibition of pro-apoptotic BAX impairs the cells' ability to initiate premature or unwanted cell death in terminally differentiated cells, including cardiomyocytes and neurons. BAX is a central mediator of both necrosis and apoptosis (17).

Myocardial infarction (MI) is a sudden event in which prolonged ischemia precipitates the deaths of myocardial cells. In ST-segment elevation MI, myocardial ischemia is precipitated by acute thrombotic occlusion of a coronary artery. In the infarct zone, necrotic deaths of cardiomyocytes and non-myocytes predominate, beginning within ~1 h of ischemia and continuing for <1 day. In addition, a delayed wave of apoptosis takes place in the pen-infarct zone peaking at ~24 h in myocardial infarction/reperfusion (MI/R). Both forms of cell death play important roles in the evolution of the infarct (1-3). Necrosis is responsible for the drastic decrease in cellularity within the infarct zone and for eliciting downstream tissue responses such as inflammation, matrix remodeling, and later fibrosis (4), and apoptosis in the pen-infarct zone is a major component of early post-infarct remodeling (5). The amount of cardiac damage over the first ~24-48 h of MI, "infarct size", is the major determinant of post-MI chronic heart failure and mortality in humans and experimental animals (6,7). As MIs are the proximate cause of ~50% of heart failure cases, therapeutic interventions to limit cardiac damage sustained over just the first 24-48 hours present an opportunity to impact the incidence of heart failure.

Current treatments for MI include: (a) drugs that reduce myocardial oxygen demand (e.g. β-adrenergic receptor blockers) (8-10); and (b) reperfusion, usually through angioplasty/stenting. While both therapies demonstrate efficacy (11-12), considerable mortality remains. The development of effective treatments has proved challenging. Unsuccessful examples include anti-oxidants such as superoxide dismutase (13), $Na^+/H^+$ exchange inhibitors (14), and various anti-neutrophil antibodies (15,16).

The present invention address the need for inhibitors of BAX that can be used to treat MI and other indications in which inhibition of premature or unwanted cell death is desirable, such as, for example, chemotherapy-induced cardiomyopathy.

SUMMARY OF THE INVENTION

The invention provides compounds having the structure of formula

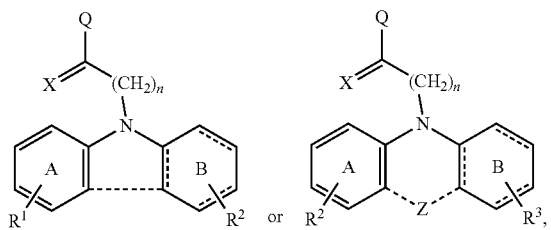

compositions comprising the compounds, and methods of using these compounds for treating a disease or disorder in which it is desirable to inhibit BAX, such as a cardiovascular disease or disorder.

DETAILED DESCRIPTION OF THE INVENTION

Figure 1:
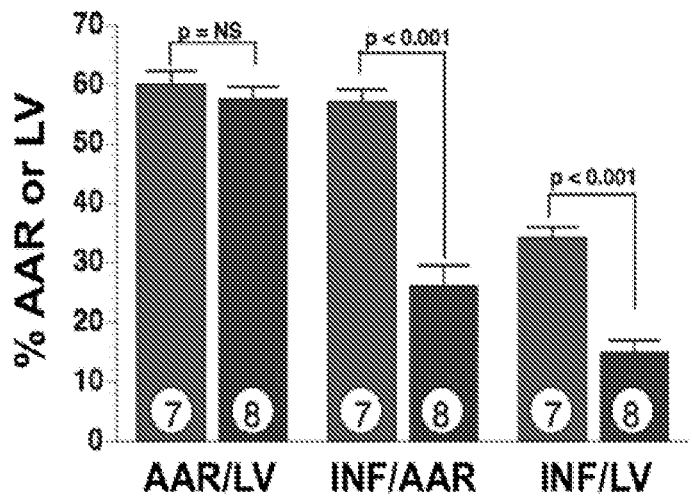
FIG. 1. Deletion of BAX in knockout mice reduces myocardial infarct size in vivo. Number of mice shown in circles. Left column in each pair represents data from wild type mice, while right column represents data from BAX knock-out mice. AAR—area at risk, INF—infarct size, LV—left ventricle.

The invention provides a method of treating a disease or condition in a subject in which it is desirable to inhibit Bcl-2-associated x-protein (BAX) comprising administering to the subject one or more of the compounds of formula (I) and/or formula (IV) in an amount effective to treat the disease or condition in a subject, wherein formula (I) and formula (IV) have the structure

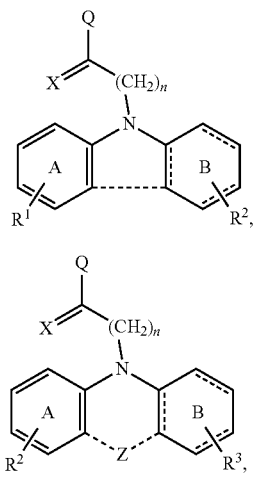

wherein
A is phenyl or a 6-membered heteroaromatic ring having 1, 2 or 3 N atoms in the heteroaromatic ring;
B is phenyl, or a 6-membered heteroaromatic ring having 1, 2 or 3 N atoms in the heteroaromatic ring; or a 6-membered aliphatic ring with up to 3 heteroatoms;
the dashed line between A and B indicates an optional bond;
R1 and R2 are independently none, C1-C5 alkyl, F, Cl, Br, I, CN, $NO_2$, NR4, $NR4_2$, OR4, $CF_3$, COOH, COOR4, NHR4, OCR4, OCOR4, OR4, SR4, SOR4, or $SO_2R4$;
X is H, $NH_2$, OH, O, F, Cl, Br, I, CN, SH, $NO_2$, NR4, $NR4_2$, OR, $CF_3$, COOH, R4, COOR4, NHR4, OCR4, OCOR4, OR4, SR4, SOR4, or $SO_2R4$; wherein the bond between X and the main scaffold is a single bond or a double bond, depending on the definition of X;
Q is

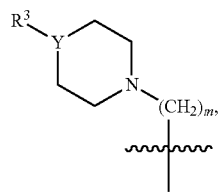

$(CH_2)_mN((CH_2)_oR5)_2$, COH, COOH, or $CH_2NH(CH_2)_lOH$
R3 is none, H, C1-C6 alkyl, R4(C=O), or $(CH_2)_pOH$;
R4 is H or C1-C3 alkyl;
each R5 is independently OH, SH, $NR4_2$ or R4;
Y is O, S, N or CH;

Z is O, S, NR4, CHR4, $S(O)_2$, $C(Me)_2$ or C(O);
each l, m, n, o and p is independently 1-3;
or a pharmaceutically acceptable salt thereof.

In one embodiment of the methods and compounds disclosed herein, the compound can have, for example, the structure of formula (II), (III), (IV) or (VI)

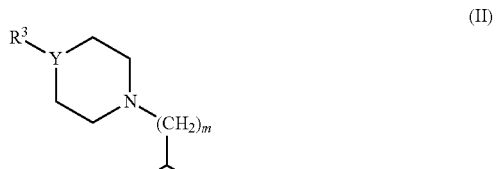

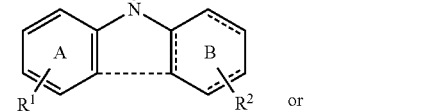

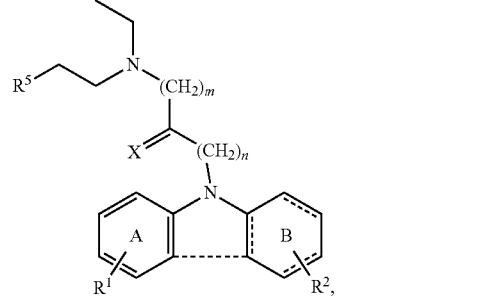

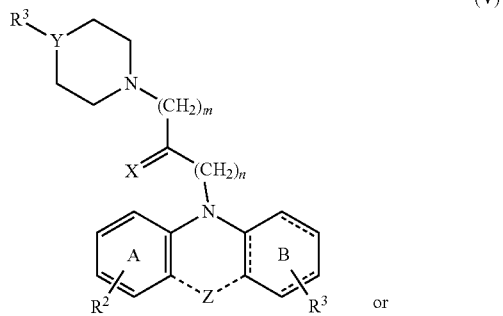

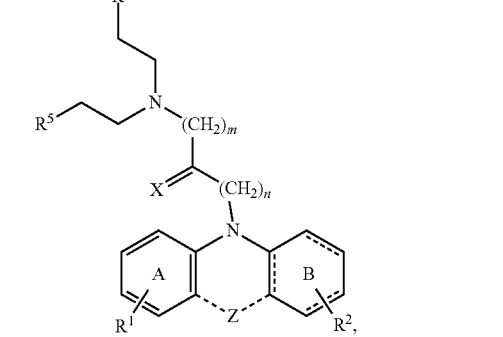

or a pharmaceutically acceptable salt thereof.

In one embodiment of the methods and compounds disclosed herein, there is no bond between A and B. In one embodiment, R1 and/or R2 are in the para position with respect to the bond to the N atom.

In one embodiment of the methods and compounds disclosed herein, the compound can have a structure, for example, selected from the group consisting of
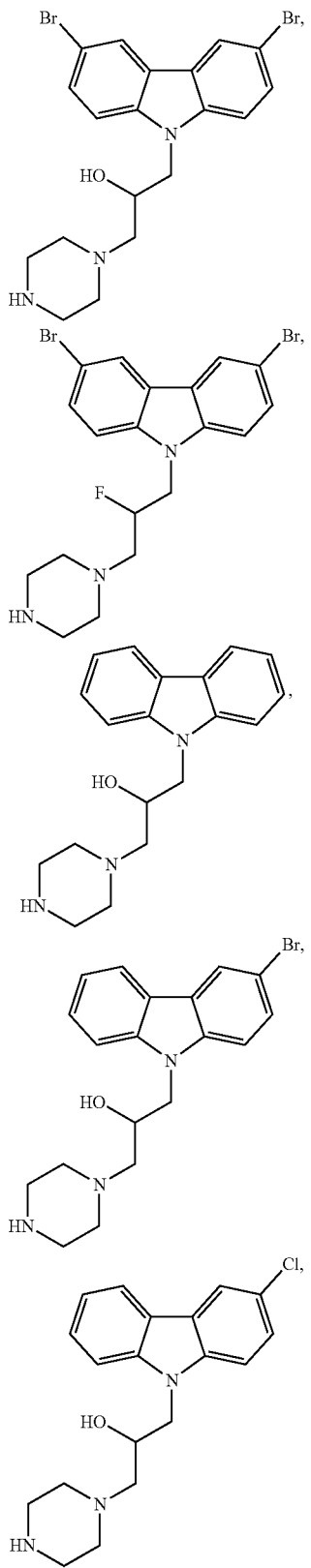
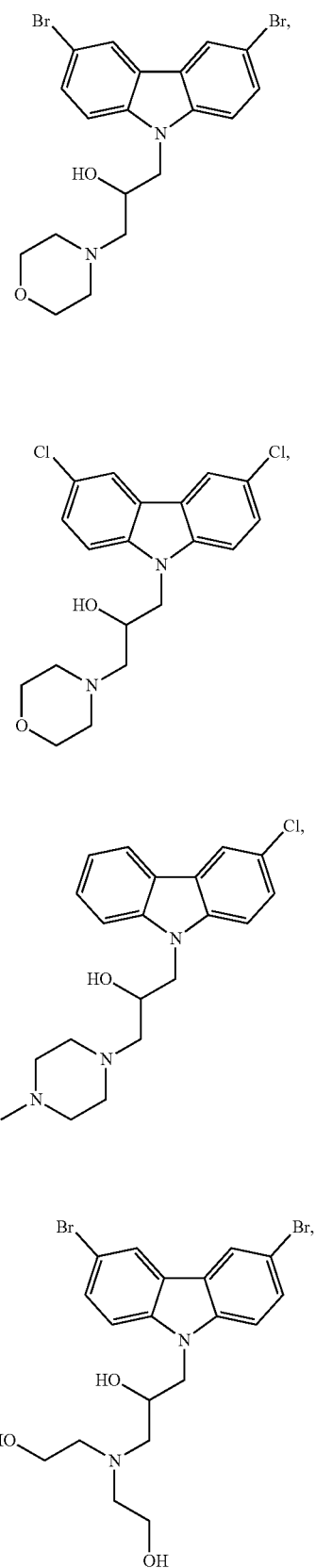

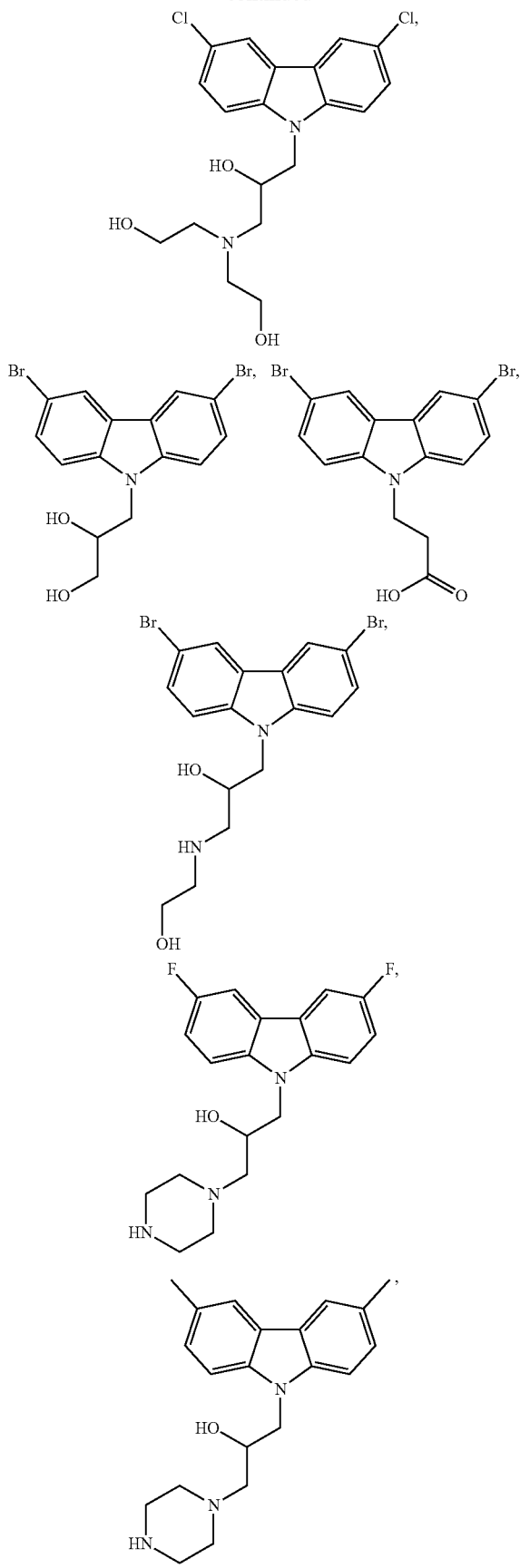

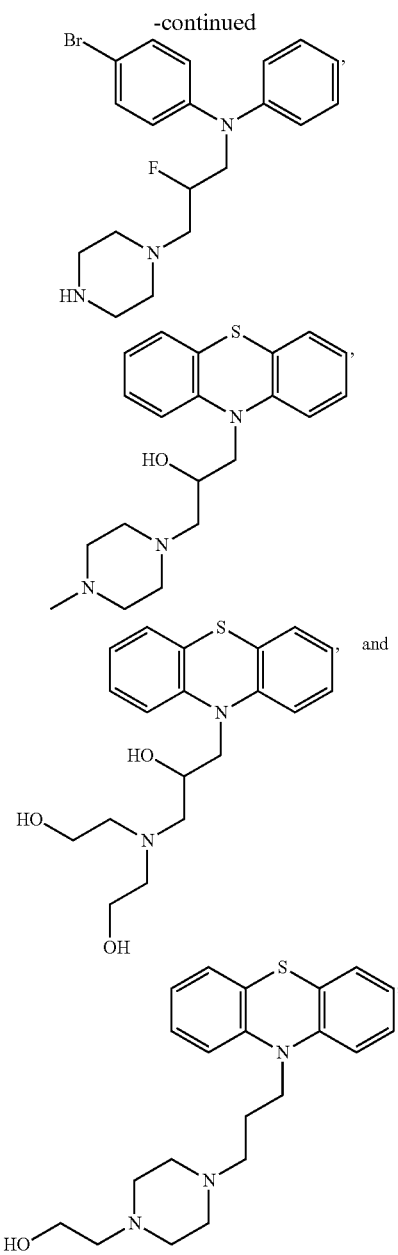

or a pharmaceutically acceptable salt thereof.

Preferably, the one or more compounds is administered in an amount effective to inhibit BAX in a subject.

The invention also provides a method of inhibiting Bcl-2-associated x-protein (BAX) in a subject comprising contacting the BAX with one or more of the compounds of formula (I) and/or formula (IV) in an amount effective to inhibit BAX, wherein formula (I) and formula (IV) have the structure as defined herein.

Also provided is a method of inhibiting Bcl-2-associated x-protein (BAX) comprising contacting BAX with one or more of any of the compounds or pharmaceutical compositions disclosed herein in an amount effective to inhibit BAX. Preferably, the BAX is in a subject, and the one or more compounds or compositions is administered to the subject.

The subject being administered the compound, and being treated, may have, for example, a disease or condition is selected from the group consisting of hypoxic cardiomyocytes, cardiac ischemia, cardiac ischemia-reperfusion injury, myocardial infarction, myocardial infarction and reperfusion injury, chemotherapy-induced cardiotoxicity, arteriosclerosis, heart failure, heart transplantation, aneurism, chronic pulmonary disease, ischemic heart disease, hypertension, pulmonary hypertension, thrombosis, cardiomyopathy, stroke, a neurodegenerative disease or disorder, an immunological disorder, ischemia, ischemia-reperfusion injury, infertility, a hematological disorder, renal hypoxia, hepatitis, a liver disease, a kidney disease, an intestinal disease, liver ischemia, intestinal ischemia, asthma, AIDS, Alzheimer's disease, Parkinson's disease, Huntington's disease, retinitis pigmentosa, spinal muscular atrophy, cerebellar degeneration, amyotrophic lateral sclerosis, organ transplant rejection, arthritis, lupus, irritable bowel disease, Crohn's disease, asthma, multiple sclerosis, diabetes, premature menopause, ovarian failure, follicular atresia, fanconi anemia, aplastic anemia, thalassemia, congenital neutropenia, myelodysplasia, and a disease or disorder involving cell death and/or tissue damage.

In the case where the disease or condition is chemotherapy-induced cardiotoxicity, preferably the compound does not interfere with the ability of the chemotherapeutic agent to treat cancer. The chemotherapeutic agent can be, for example, one or more of doxorubicin and trastuzumab. The cancer can be, for example, one or more of a leukemia, a solid tumor, acute lymphoblastic leukemia (ALL), acute myeloid leukemia (AML), chronic lymphocytic leukemia (CLL), chronic myeloid leukemia (CML), breast cancer, prostate cancer, lymphoma, skin cancer, pancreatic cancer, colon cancer, melanoma, malignant melanoma, ovarian cancer, brain or spinal cord cancer, primary brain carcinoma, medulloblastoma, neuroblastoma, glioma, head-neck cancer, glioma, glioblastoma, liver cancer, bladder cancer, stomach cancer, kidney cancer, placental cancer, cancer of the gastrointestinal tract, non-small cell lung cancer (NSCLC), head or neck carcinoma, breast carcinoma, endocrine cancer, eye cancer, genitourinary cancer, cancer of the vulva, ovary, uterus or cervix, hematopoietic cancer, myeloma, leukemia, lymphoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, chronic granulocytic leukemia, acute granulocytic leukemia, acute myelogenous leukemia, chronic myelogenous leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft tissue cancer, soft-tissue sarcoma, osteogenic sarcoma, sarcoma, primary macroglobulinemia, central nervous system cancer and retinoblastoma.

Also provided is a method of treating a myocardial infarction or a myocardial infarction and reperfusion injury in a subject comprising administering to the subject one or more of the compounds or pharmaceutical compositions disclosed herein in an amount effective to treat a myocardial infarction or a myocardial infarction and reperfusion injury in a subject in need thereof. Preferably, the one or more compounds or the pharmaceutical composition is administered in an amount effective to inhibit Bcl-2-associated x-protein (BAX) in a subject.

The subject can be, for example, a mammal, and is preferably a human.

As used herein, "treating" or to "treat" a disease or disorder means to alleviate or ameliorate or eliminate a sign or symptom of the disease or disorder that is being treated. When the compound or composition is administered to a subject before or at the onset of a disease or disorder, the compound or composition can prevent or reduce the severity of the disease or disorder. For example, administration of the compound to a subject can prevent or reduce the severity of chemotherapy-induced cardiotoxicity that would occur in the absence of administration of the compound. Administration of the compound can include preventive and/or therapeutic administration.

The compounds and compositions of the present invention can be administered to subjects using routes of administration known in the art. The administration can be systemic or localized to a specific site. Routes of administration include, but are not limited to, intravenous, intramuscular, intrathecal or subcutaneous injection, oral or rectal administration, and injection into a specific site.

Preferably, the compounds and compositions disclosed herein are administered acutely to treat a disease or disorder, due to potential hazards of long-term inhibition of cell death, e.g. cancer. The therapy can be used in conjunction with effective existing therapies for treating the disease or disorder, such as, e.g., angioplasty/stenting for cardiovascular disease.

The invention provides a compound having the structure of formula (VII)

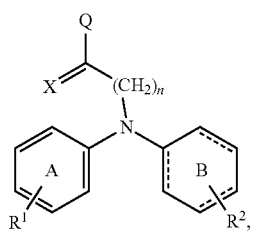

(VII)

wherein

A is phenyl or a 6-membered heteroaromatic ring having 1, 2 or 3 N atoms in the heteroaromatic ring;

B is phenyl, or a 6-membered heteroaromatic ring having 1, 2 or 3 N atoms in the heteroaromatic ring; or a 6-membered aliphatic ring with up to 3 heteroatoms;

R1 and R2 are independently none, C1-C5 alkyl, F, Cl, Br, I, CN, $NO_2$, NR4, $NR4_2$, OR4, $CF_3$, COOH, COOR4, NHR4, OCR4, OCOR4, OR4, SR4, SOR4, or $SO_2R4$;

X is H, $NH_2$, OH, O, F, Cl, Br, I, CN, SH, $NO_2$, NR4, $NR4_2$, OR, $CF_3$, COOH, R4, COOR4, NHR4, OCR4, OCOR4, OR4, SR4, SOR4, or $SO_2R4$; wherein the bond between X and the main scaffold is a single bond or a double bond, depending on the definition of X;

Q is

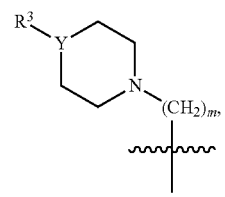

$(CH2)_mN((CH_2)_oR5)_2$, COH, COOH, or $CH_2NH(CH_2)_lOH$;
R3 is none, H, C1-C6 alkyl, R4(C=O), or $(CH_2)_pOH$;
R4 is H or C1-C3 alkyl;
each R5 is independently OH, SH, $NR4_2$ or R4;
Y is O, S, N or CH;
each l, m, n, o and p is independently 1-3;
or a pharmaceutically acceptable salt thereof.

The compound can have, for example, the structure of formula (VIII) or (IX)

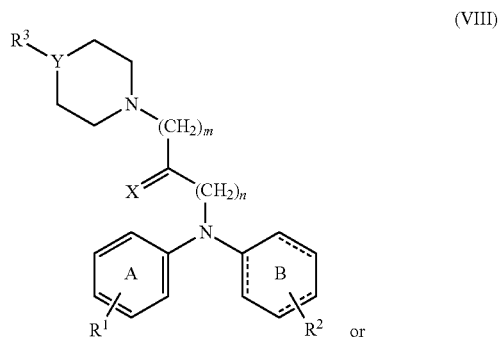

(VIII)

or

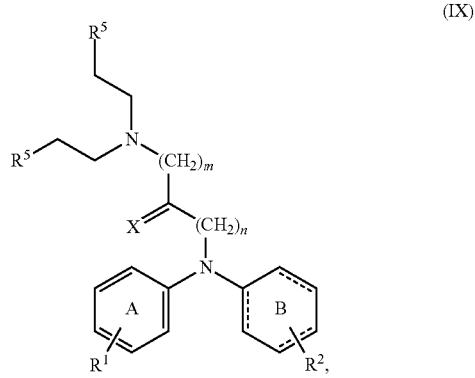

(IX)

or a pharmaceutically acceptable salt thereof.

The compound can have, for example, a structure selected from the group consisting of

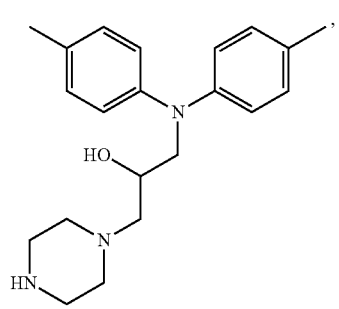

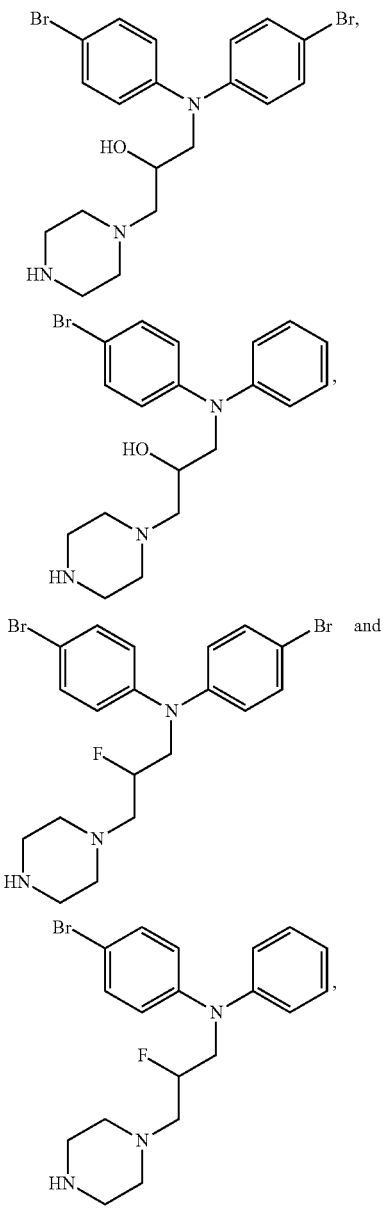

or a pharmaceutically acceptable salt thereof.

The invention also provides a compound having the structure of formula (X) or (XI)

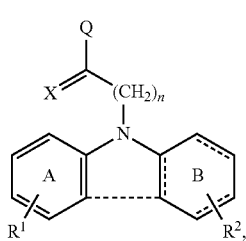
(X)

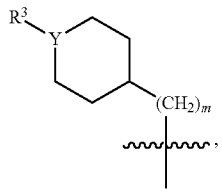
(XI)

wherein
A is phenyl or a 6-membered heteroaromatic ring having 1, 2 or 3 N atoms in the heteroaromatic ring;
B is phenyl, or a 6-membered heteroaromatic ring having 1, 2 or 3 N atoms in the heteroaromatic ring; or a 6-membered aliphatic ring with up to 3 heteroatoms;
with the proviso that at least one of A and B is not phenyl;
the dashed line between A and B indicates an optional bond;
R1 and R2 are independently none, C1-C5 alkyl, F, Cl, Br, I, CN, $NO_2$, NR4, $NR4_2$, OR4, $CF_3$, COOH, COOR4, NHR4, OCR4, OCOR4, OR4, SR4, SOR4, or $SO_2R4$;
X is H, $NH_2$, OH, O, F, Cl, Br, I, CN, SH, $NO_2$, NR4, $NR4_2$, OR, $CF_3$, COOH, R4, COOR4, NHR4, OCR4, OCOR4, OR4, SR4, SOR4, or $SO_2R4$; wherein the bond between X and the main scaffold is a single bond or a double bond, depending on the definition of X;
Q is $$\begin{array}{c} R^3\text{—}Y \\ \diagup \\ \diagdown \\ (CH_2)_m \\ \text{\textasciitilde\textasciitilde\textasciitilde}|\text{\textasciitilde\textasciitilde\textasciitilde} \end{array}$$, $(CH_2)_m N(CH_2)_o R5)_2$, COH, COOH, or $CH_2NH(CH_2)_l OH$;
R3 is none, H, C1-C6 alkyl, R4(C=O), or $(CH_2)_p OH$;
R4 is H or C1-C3 alkyl;
each R5 is independently OH, SH, $NR4_2$ or R4;
Y is O, S, N or CH;
Z is O, S, NR4, CHR4, $S(O)_2$, $C(Me)_2$ or C(O);
each l, m, n, o and p is independently 1-3;
or a pharmaceutically acceptable salt thereof.

In one embodiment, Z is O, NR4, CHR4, $S(O)_2$, $C(Me)_2$ or C(O).

Pharmaceutically acceptable salts that can be used with compounds of the present invention include, e.g., non-toxic salts derived, for example, from inorganic or organic acids including, but not limited to, salts derived from hydrochloric, sulfuric, phosphoric, acetic, lactic, fumaric, succinic, tartaric, gluconic, citric, methanesulphonic and p-toluenesulphonic acids.

The invention also provides a pharmaceutical composition comprising one or more of the compounds disclosed herein and a pharmaceutically acceptable carrier. Pharmaceutically acceptable carriers and diluents that can be used herewith encompasses any of the standard pharmaceutical carriers or diluents, such as, for example, a sterile isotonic saline, phosphate buffered saline solution, water, and emulsions, such as an oil/water or water/oil emulsions. The pharmaceutical compositions can be formulated to be advantageous for the selected route of administration to a subject.

As used herein, "BAX" is Bcl-2-associated x-protein. In an embodiment, the BAX is mammalian. In a preferred embodiment, the BAX is a human BAX. In an embodiment, the BAX comprises consecutive amino acid residues having the following sequence:

```
                                                  (SEQ ID NO: 1)
MDGSGEQPRGGGPTSSEQIMKTGALLLQGFIQDRAGRMGGEAPELALDPV

PQDASTKKLSECLKRIGDELDSNMELQRMIAAVDTDSPREVFFRVAADMF

SDGNFNWGRVVALFYFASKLVLKALCTKVPELIRTIMGWTLDFLRERLLG

WIQDQGGWDGLLSYFGTPTWQTVTIFVAGVLTASLTIWKKMG.
```

As used herein, small molecule BAX inhibitors are defined as compounds that bind to BAX and inhibit its function.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Details

BAX is a Therapeutic Target for MI/R

To determine whether BAX provides a therapeutic target for MI/R in vivo, wild type and BAX knockout (KO) mice were subjected to 45 min ischemia/24 h reperfusion. These KO mice have a generalized deletion of BAX making them a good model for the antagonism of BAX in both cardiomyocytes and non-myocytes. Area at risk (AAR) was measured by Evans blue dye and infarct size by tetrazolium chloride (TTC) staining (FIG. 1). Consistent with a previous study in isolated hearts (18), BAX deletion markedly reduced infarcts indicating that BAX plays an important role in the pathogenesis of infarction in vivo. These KO mice have a generalized deletion of BAX making them a good model for the antagonism of BAX in both cardiomyocytes and non-myocytes.

Identification of a Small Molecule Inhibitor of BAX

Figure 2:
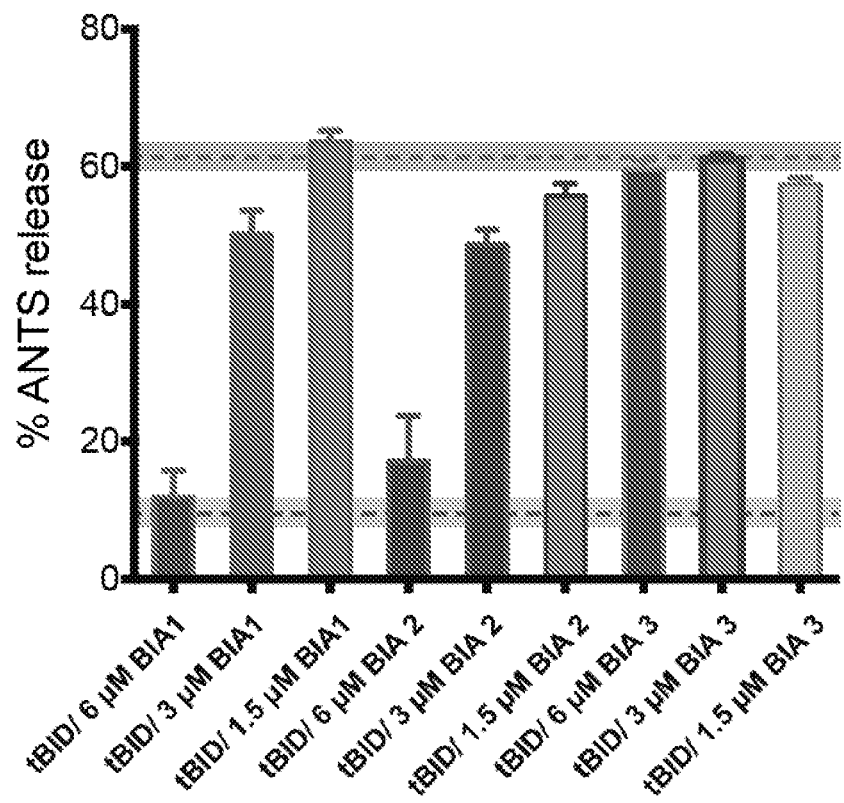
FIG. 2. Compounds BAI-1 and BAI-2 inhibit membrane permeabilization induced by tBID-activated BAX. Maximum permeabilization of tBID-induced BAX activation was recorded at ~60%. Maximum permeabilization of BAX alone was recorded at ~10%. Another compound, BAI-3, was not effective to inhibit tBID-induced BAX activation. tBID, BAI-1, BAI-2, and BAI-3 alone do not stimulate fluorophore release (not shown). Structures of BAI-1 and BAI-2 are illustrated in FIG. 3A; structure of BAI-3 shown in FIG. 3C.
Figure 3A:
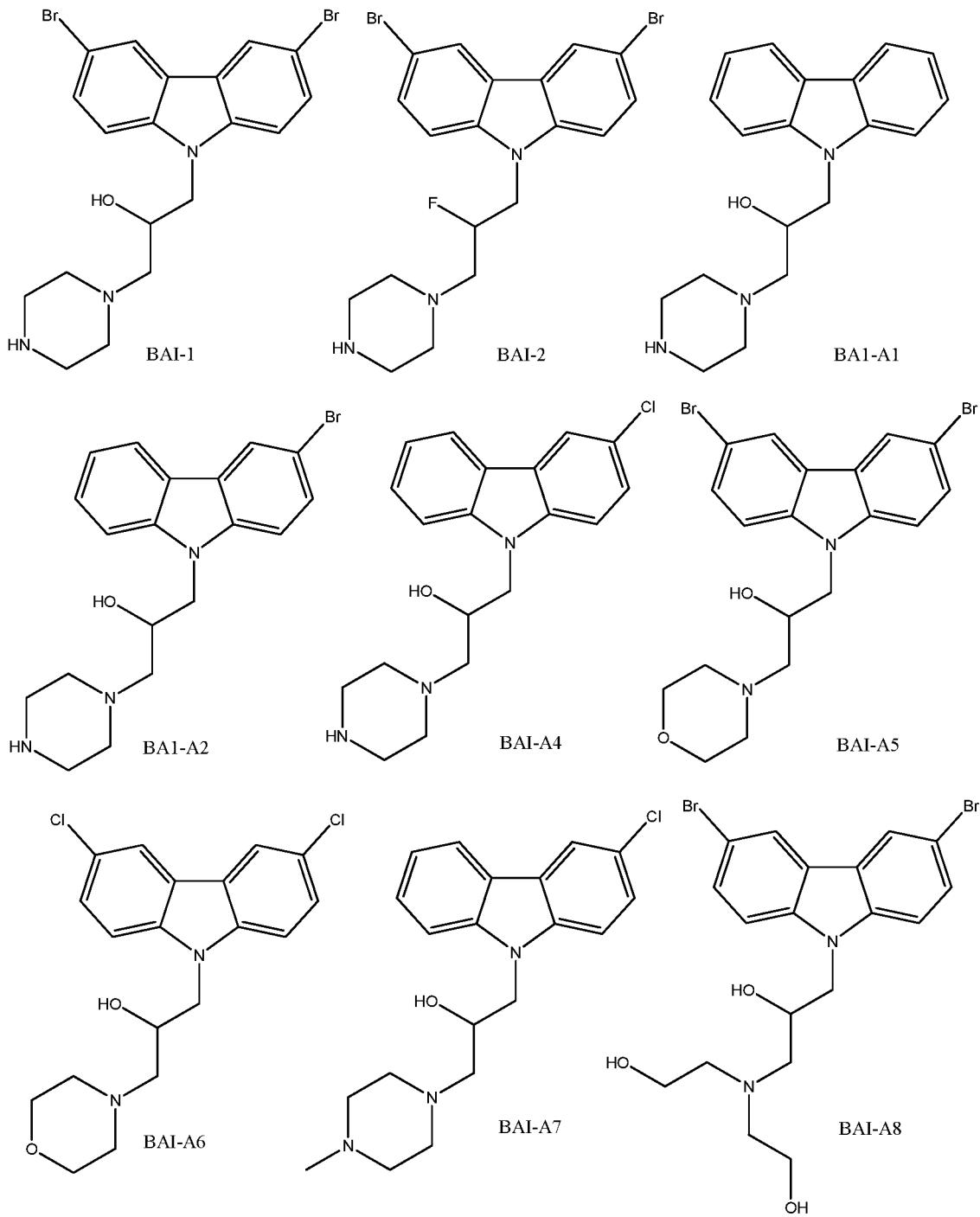
FIG. 3A-3C. Structures of compounds.

Previously, a small molecule screen using isolated mitochondria, revealed compounds that inhibit tBID-induced cytochrome c release. These compounds were hypothesized, but never shown, to work through BAX inhibition (19, 20). Accordingly, it was first investigated whether several of these small molecules inhibit BAX-mediated permeabilization of artificial membranes of similar lipid composition to the outer mitochondrial membrane (OMM). A liposome release assay (21), in which liposomes that contain a fluorophore are created, was used. Incorporation of tBID-activated BAX into the liposome membrane stimulates release of the fluorophore, providing a system to study BAX-mediated membrane permeabilization in isolation of other mitochondrial and cellular factors. Using this assay, a lead small molecule, termed BAX Activation Inhibitor 1 (BAI-1) (FIG. 3A), was shown to inhibit liposomal release of fluorophore in a dose-dependent and BAX-dependent manner (FIG. 2). Moreover, another compound, BAI-2, inhibited BAX-induced liposomal release (FIG. 2). These results indicate that inhibition of tBID-induced cytochrome c release from mitochondria by BAI-1 involves antagonism of BAX.

Figure 5:
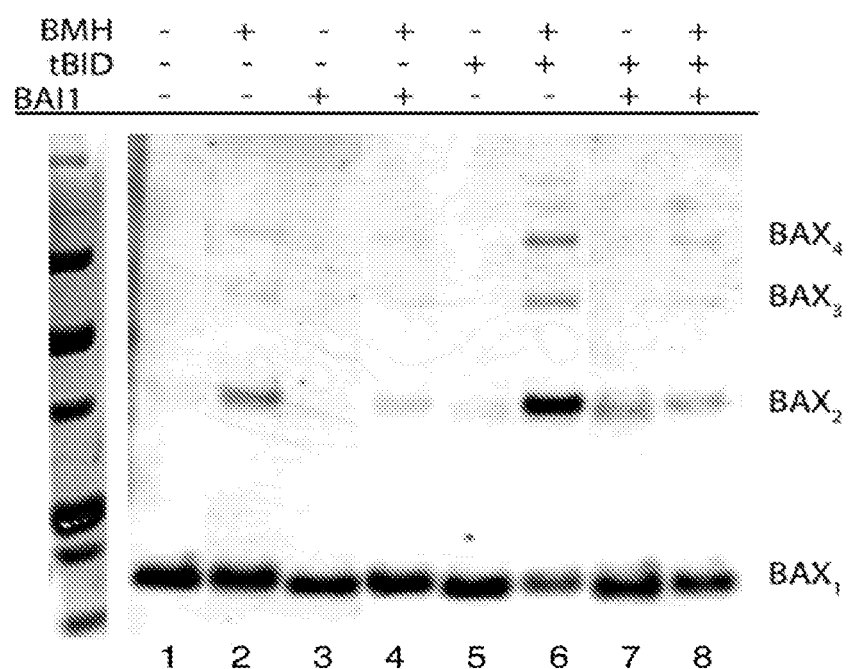
FIG. 5. Effects of BAI-1 on tBID-induced BAX oligomerization.

Next, it was tested whether BAI-1 binds to recombinant, purified BAX using 1H-NMR, and this was found to be the case (data not shown). To identify the mechanism of BAI-1 binding to BAX, $^{15}$N-$^{1}$H HSQC NMR analysis of BAX was performed upon titration of BAI-1. BAI-1 induced significant chemical shift perturbations on HSQC spectra of BAX, which were localized in the region formed by α-helices 3, 4, and 5 and the loop between α-helices 3 and 4 (data not shown). A few chemical shift changes in other regions of the structure were not localized and occurred predominantly in hydrophobic residues at the hydrophobic core of the BAX structure. These NMR data highlight a binding site for BAI-1 in a region of the BAX structure distinct from the trigger site and for which information does not currently exist regarding effects on BAX activation. To identify precisely how BAI-1 binds to and inhibits BAX, NMR data were used to guide molecular docking studies. FIG. 5 shows a close-up view of the novel BAX binding site and the bound docked structure of BAI-1.

It was hypothesized that BAI-1 stabilizes the interactions among these helices and the BAX structure and, through this mechanism, inhibits BAX conformational activation by BH3-only proteins. To assess inhibition of BAX activation by BAI-1, BAX oligomerization (which is downstream of activation) was tested using immunoblotting after cross-linking with BMH (FIG. 5). BAI-1 inhibited tBID-induced BAX oligomerization (lane 8 versus lane 6). Since BAI-1 does not inhibit the binding of BH3-only activator proteins to BAX (not shown), the most likely model is that BAI-1 functions as an allosteric inhibitor of BAX activation.

BAI-1 Mechanism of Action

A key event in BAX activation is exposure of α helix 9 containing a transmembrane domain that inserts tightly into the outer mitochondrial membrane (OMM). BAX insertion into the OMM can be assessed by treating isolated mitochondria with strong alkali, which separates loosely attached proteins from mitochondria but fails to extract membrane-inserted proteins. Staurosporine (STS) treatment of mouse embryonic fibroblasts resulted in a pool of BAX that could not be retrieved by treatment of isolated mitochondria with strong alkali. Treatment of cells with BAI-1 significantly decreased the inserted pool. These data indicate that BAI-1 inhibits STS-induced exposure of BAX α helix 9. One important result of BAX conformational activation is its translocation from cytosol to mitochondria. Thus, it was also evaluated whether BAI-1 can inhibit STS-induced BAX translocation. Translocation was assessed by immunostaining for mitochondrial BAX puncta. BAI-1 significantly decreased BAX translocation to the mitochondria in a dose-dependent fashion. A similar result was observed with BAI-A22. (Data not shown.)

BAI-1 Inhibits Apoptotic Cell Death and Necrotic Cell Death

Figure 14:
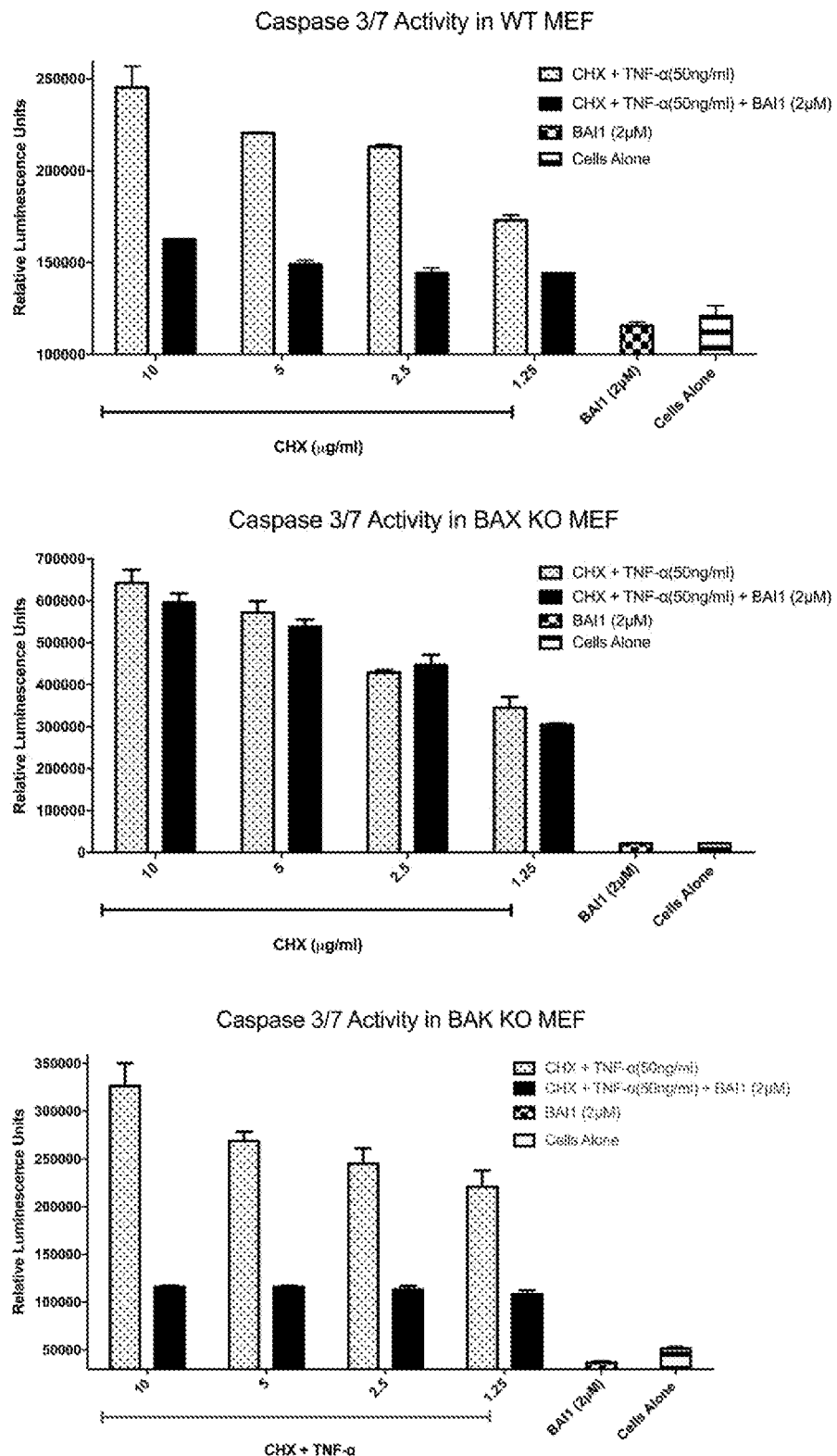
FIG. 14. BAI-1 inhibits TNFα-induced BAX-mediated apoptotic cell death in mouse embryonic fibroblasts. Inhibition of BAI-1 required BAX but not BAK.
Figure 15:
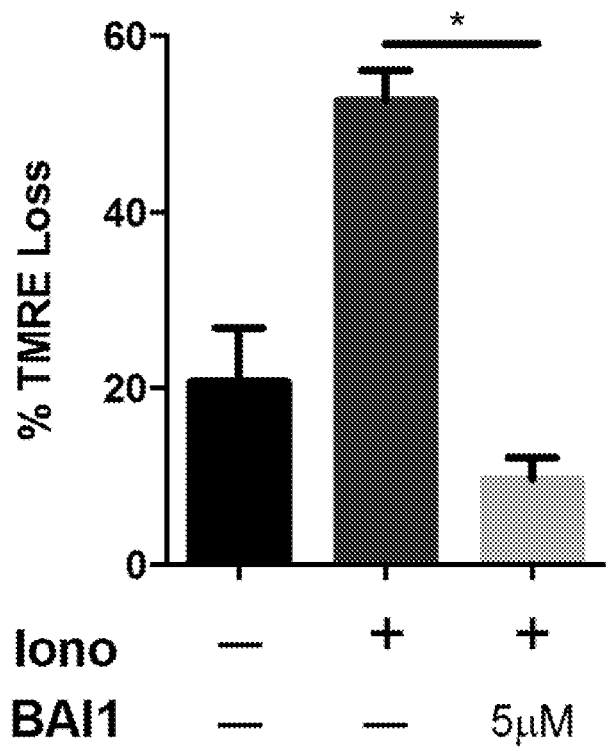
FIG. 15. BAI-1 inhibits Ionomycin-induced BAX-mediated necrotic cell death in mouse embryonic fibroblasts as measured by the loss of TMRE fluorescence using FACS analysis.

BAI-1 inhibits TNFα-induced BAX-mediated apoptotic cell death in mouse embryonic fibroblasts (FIG. 14). Inhibition of BAI-1 required BAX but not BAK. Nuclear fragmentation was also inhibited, as shown using BAI-1 and BAI-A22; externalization of phosphatidylserine was reduced as shown using BAI-1 (data not shown). BAI-1 also inhibits Ionomycin-induced BAX-mediated necrotic cell death in mouse embryonic fibroblasts as measured by the loss of TMRE fluorescence using FACS analysis (FIG. 15).

BAI-1 Inhibits Cardiomyocyte Death

Figure 6A:
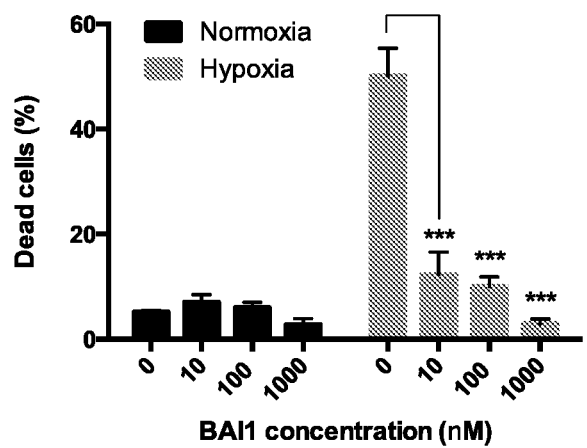
FIG. 6A-6C. BAI-1 potently inhibits primary (A) neonatal and (B) adult cardiomyocyte death induced by hypoxia and hypoxia/reoxygenation (H/R), respectively. Cell death was assessed using calcein AM (alive) and ethidium homodimer (dead) staining. (C) BAI1 inhibits hypoxia-induced loss of inner mitochondrial membrane potential ($\Delta\psi m$) in neonatal cardiomyocytes.
Figure 6B:
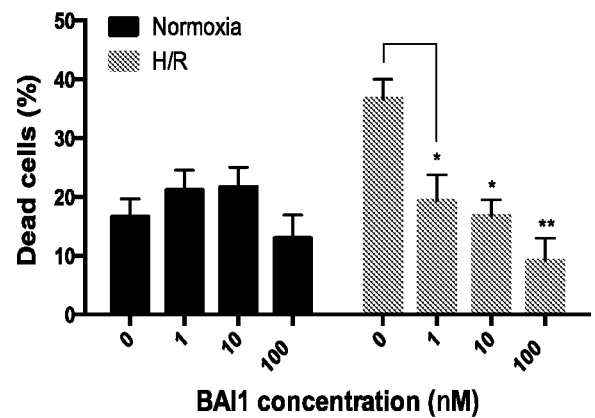
Figure 6C:
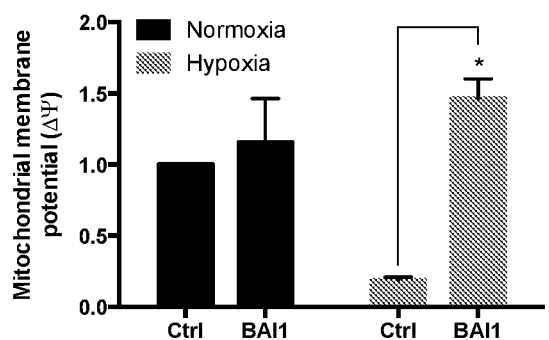
Figure 13:
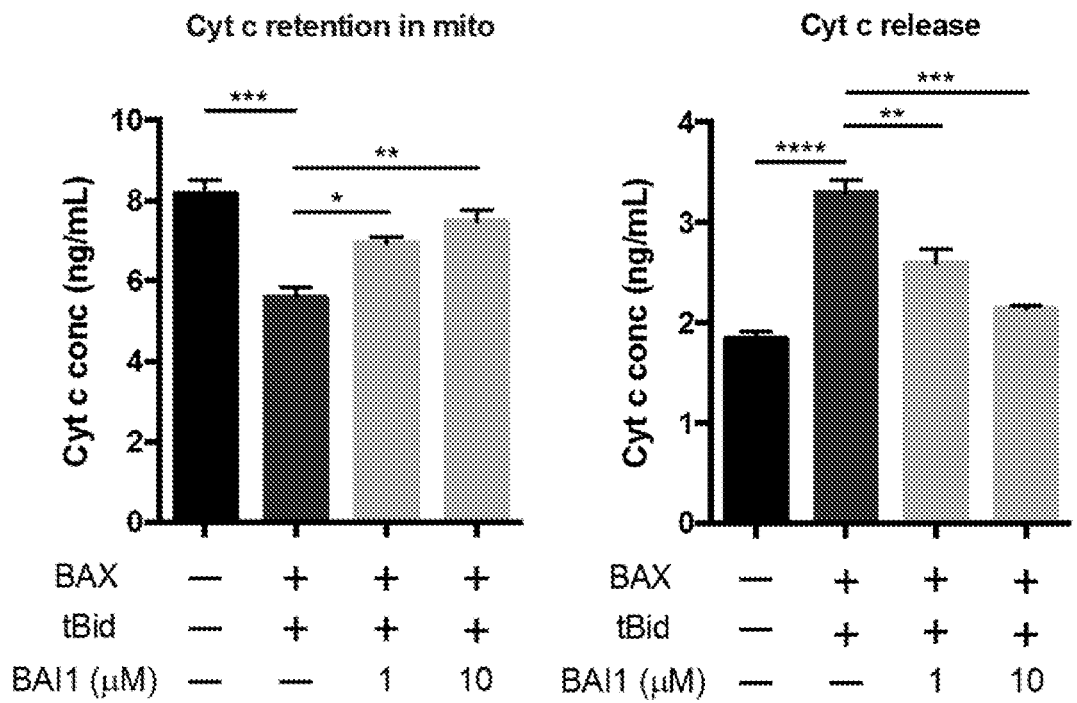
FIG. 13. BAI-1 inhibits tBID-induced BAX mediated cytochrome c release from isolated cardiac mitochondria. The levels of cytochrome c were quantified in mitochondrial and soluble fractions after incubation of mitochondria with tBID, BAX without and with BAI-1.
Figure 16:
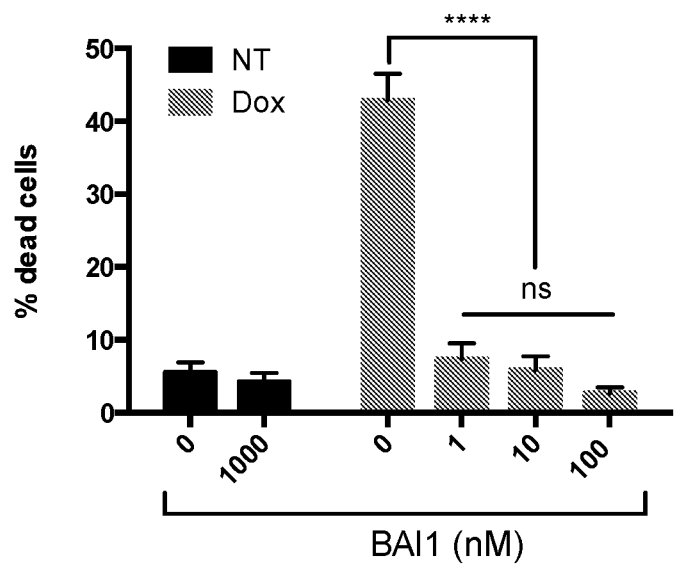
FIG. 16. BAI-1 inhibits doxorubicin-induced cell death in rat neonetal cardiomyocytes. Cell death was assessed using calcein AM (alive) and ethidium homodimer (dead) staining.
Figure 17:
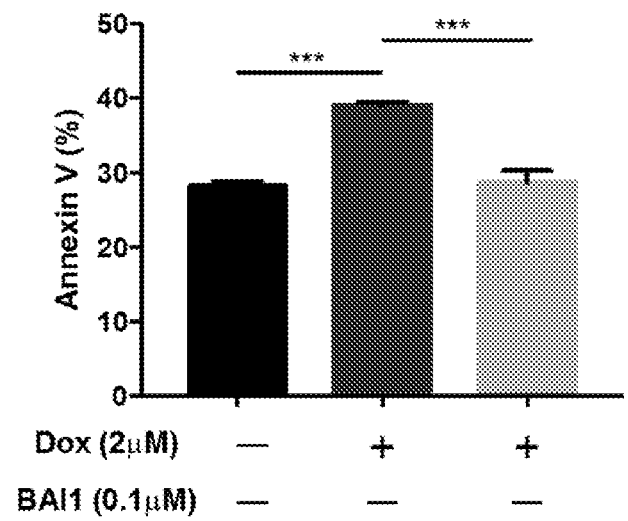
FIG. 17. BAI-1 inhibits doxorubicin-induced cell death in human cardiomyocytes derived from human induced pluripotent stem cells. Cell death was assessed using annexin V staining.
Figure 20A:
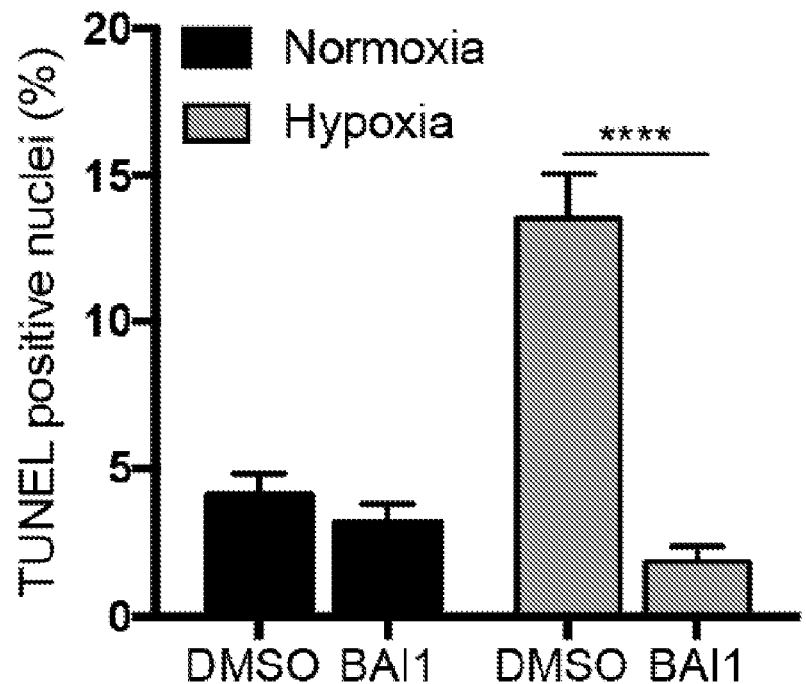
FIG. 20A-20B. BAI-1 inhibits cardiomyocyte apoptosis and necrotic cell death. (A) TUNEL assay was used to measure apoptosis in neonatal rat cardiomyocytes (NRCM) under normoxia and hypoxia with or without 1 µM BAI-1. Quantification of percentage of TUNEL positive cells. (B) NRCM were pre-treated with varying concentrations of BAI-1 and cultured under normoxic or hypoxic conditions. BAI-1 dose response. Percentage of dead cells represents percentage of ethidium homodimer-1 (EthD) positive cells.
Figure 20B:
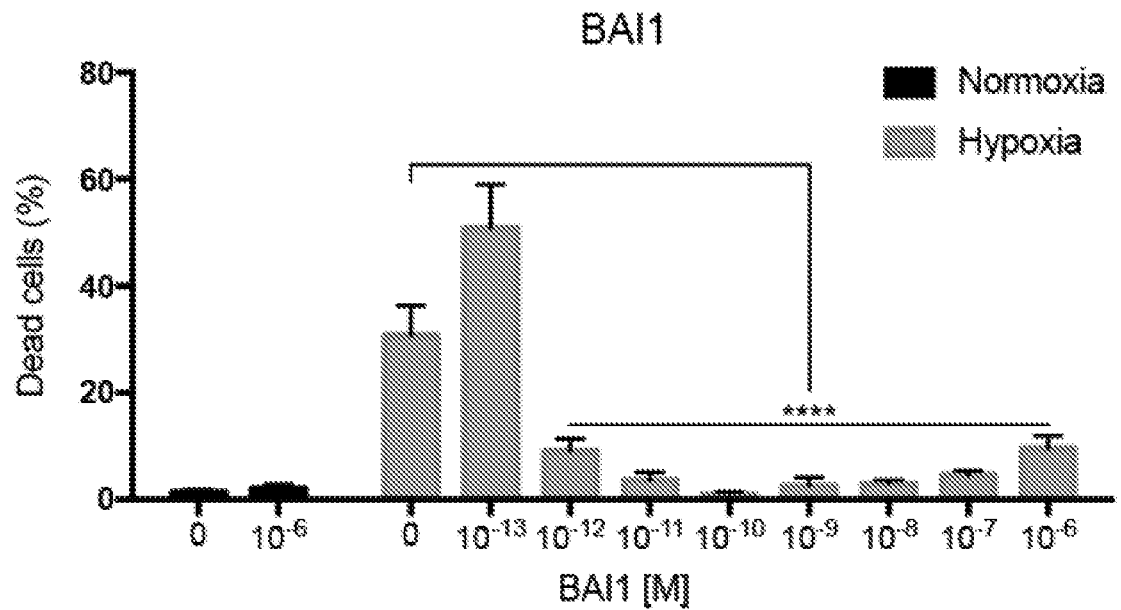
Figure 23:
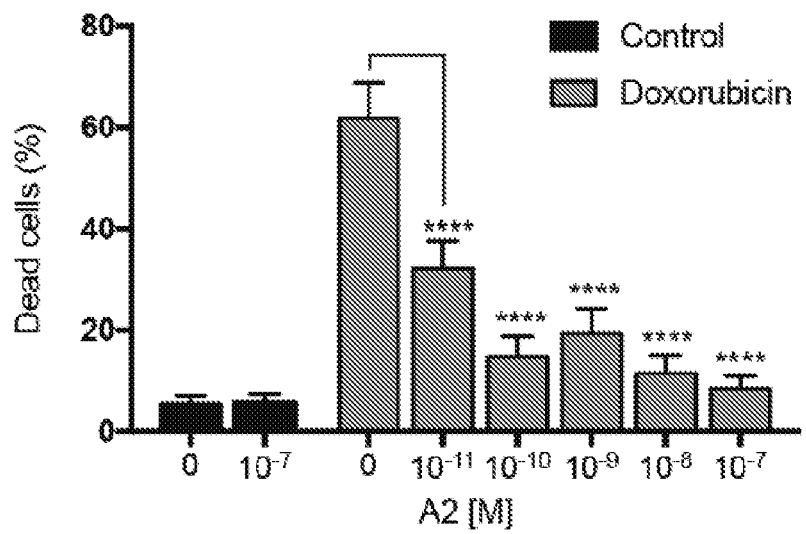
FIG. 23. BAI-A2 inhibits doxorubicin-induced cardiomyocyte necrosis. NRCM were pre-treated with varying concentrations of A2 and then stimulated with 10 µM doxorubicin for 18 hr. A2 dose response. Percentage of dead cells represents percentage of EthD positive cells.

It was tested if BAI-1 can inhibit cell death in cardiomyocytes challenged with a noxious stimuli relevant to MI/R. At ~10 nM concentrations, BAI-1 inhibited cell death in neonatal and adult cardiomyocytes challenged with 18 h of 3% hypoxia and 1 h hypoxia/2 h reoxygenation, respectively, both effects occurring in a dose-dependent manner (FIG. 6A,B). To explore the mechanism by which BAI-1 inhibits cardiomyocyte death, TMRM staining was used to assess its effect on loss of inner mitochondrial membrane potential ($\Delta\psi m$), which occurs with opening of the mPTP. BAI-1 markedly inhibited loss of $\Delta\psi m$ (FIG. 6C). BAI-1 also inhibits tBID-induced BAX mediated cytochrome c release from isolated cardiac mitochondria. The levels of cytochrome c were quantified in mitochondrial and soluble fractions after incubation of mitochondria with tBID, BAX without and with BAI-1 (FIG. 13). It was also demonstrated that BAI-1 inhibits doxorubicin-induced cell death in rat neonetal cardiomyocytes (FIG. 16) and that BAI-1 inhibits doxorubicin-induced cell death in human cardiomyocytes derived from human induced pluripotent stem cells (FIG. 17). These data demonstrate that BAI-1 potently inhibits neonatal and adult cardiomyocyte death and that mitochondrial mechanisms are involved. BAI-1 inhibits cardiomyocyte apoptosis and necrotic cell death (FIG. 20A-B). BAI-A2 was also tested and shown to inhibit doxorubicin-induced cardiomyocyte necrosis (FIG. 23).

BAI-A1 Inhibits BAX During MI/R In Vivo

Figure 7:
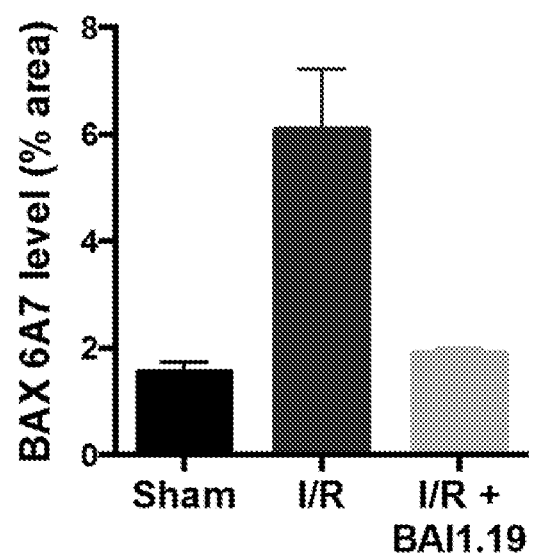
FIG. 7. BAI-A19 inhibition of BAX activation in vivo assayed with 6A7 antibody staining.

While BAI-1 potently inhibited cell death in isolated cardiomyocytes, it was discovered that BAI-1 is 99.9% bound to plasma proteins in mouse plasma (not shown). Based on its chemical structure, BAI-1 was re-engineered by removing both bromines to lower its hydrophobicity and, thereby, reduce its plasma protein binding. The resulting BAI-A1 (FIG. 3A) exhibited 89.4% plasma protein binding. As expected from the hypothesized role of the bromines in the BAI-1-BAX interaction, BAI-A1 exhibited less BAX binding than BAI-1 (not shown). Despite this, its ability to protect neonatal and adult cardiomyocytes against hypoxia and hypoxia/reoxygenation was only modestly decreased (not shown). Accordingly, the ability of BAI-A1 to inhibit BAX activation during MI/R was tested in vivo (FIG. 7). BAI-A1 potently blocks BAX conformational activation as assessed by immunostaining with 6A7, an antibody that recognizes only the active conformer of BAX. This was assessed following 45 min ischemia/6 h reperfusion, the time point that BAX is activated maximally in the absence of drug. It was concluded that BAI-A1 can access myocardial cells and is effective at inhibiting BAX activation during MI/R in vivo. The pharmacokinetics of BAI-A1 were measured in the mouse by injecting 1 mg/kg into a cohort of mice and harvesting plasma and heart tissue 0, 1, 6, and 24 h. The half-life of BAI-A1 was ~3.5 h in both plasma and heart tissue.

Studies with Additional Compounds

Figure 3B:
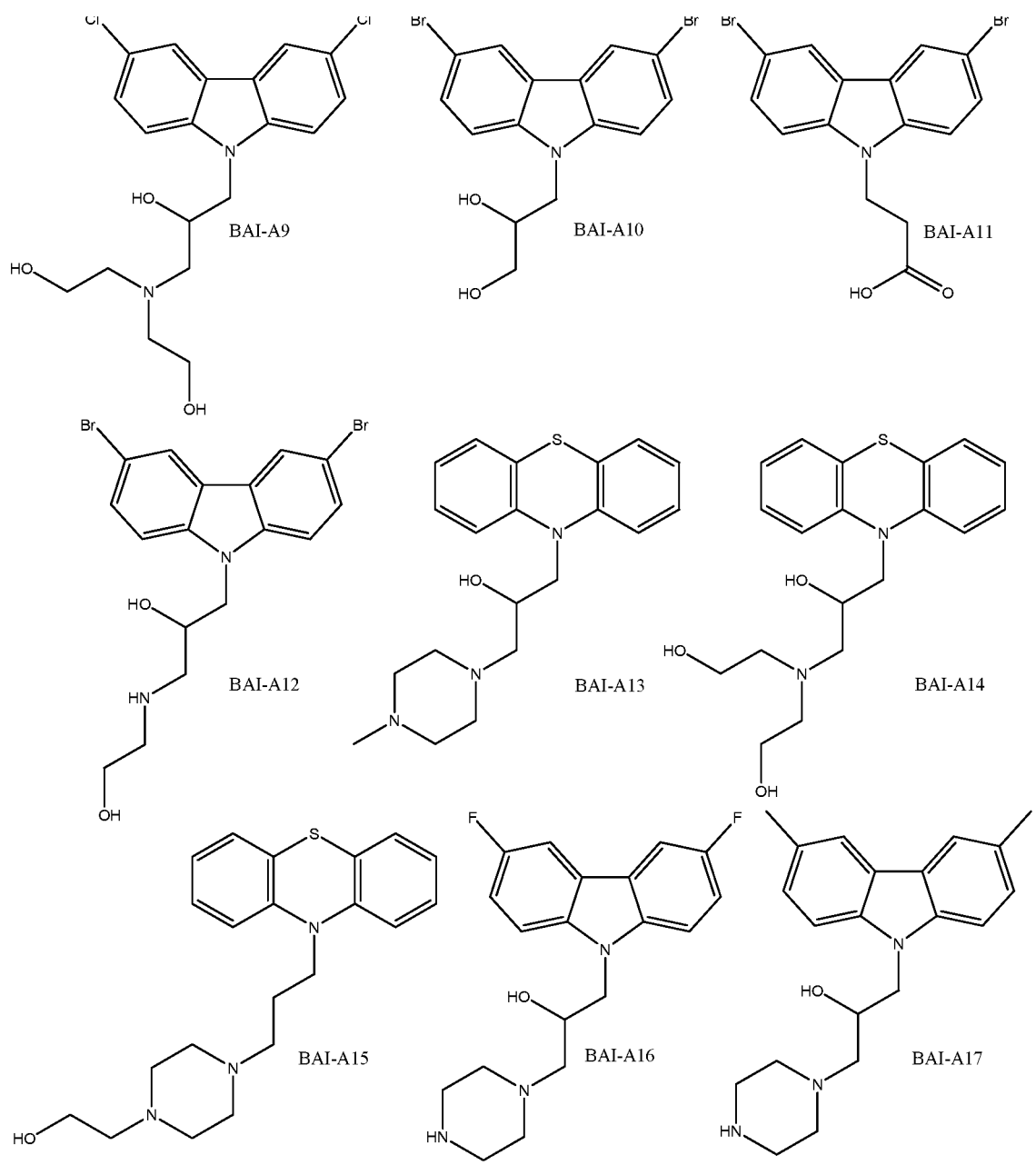
Figure 3C:
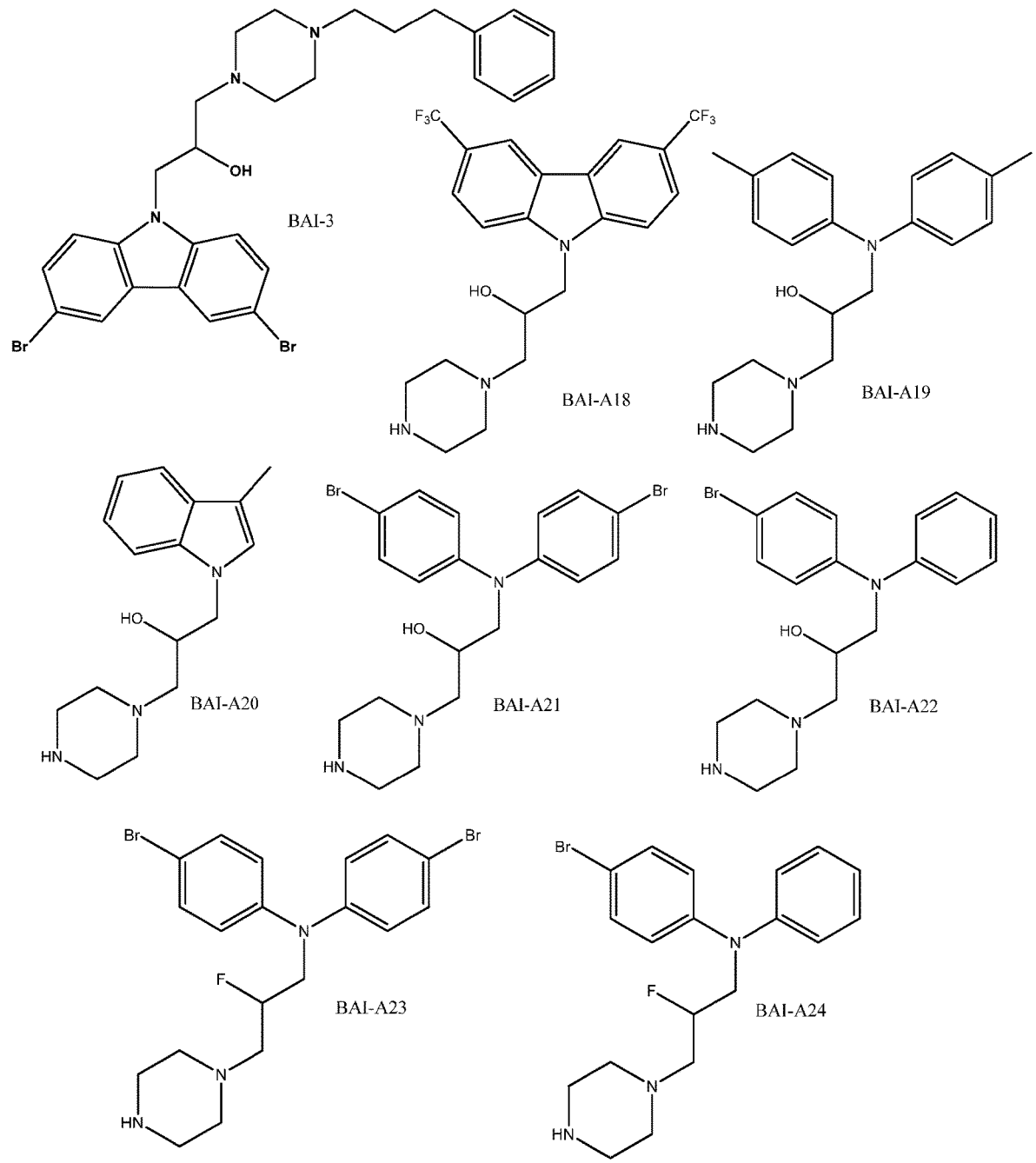
Figure 4:
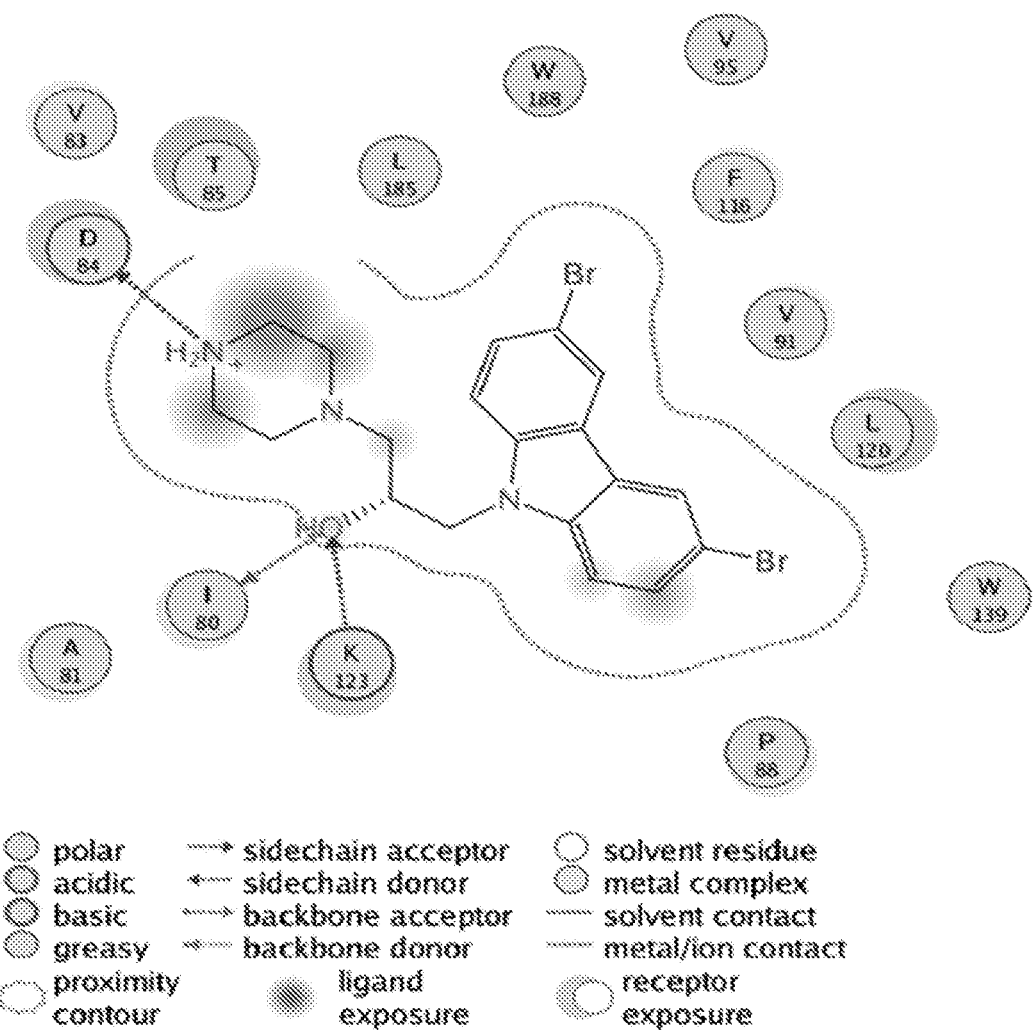
FIG. 4. NMR CSP-guided docking of BAI-1 with the BAX monomer structure using Glide (Shrodinger). BAI-1 molecules form a number of hydrophobic contacts, cation-π and electrostatic interactions in the proposed binding site, stabilizing interactions of the hydrophobic core of the BAX structure.
Figure 8:
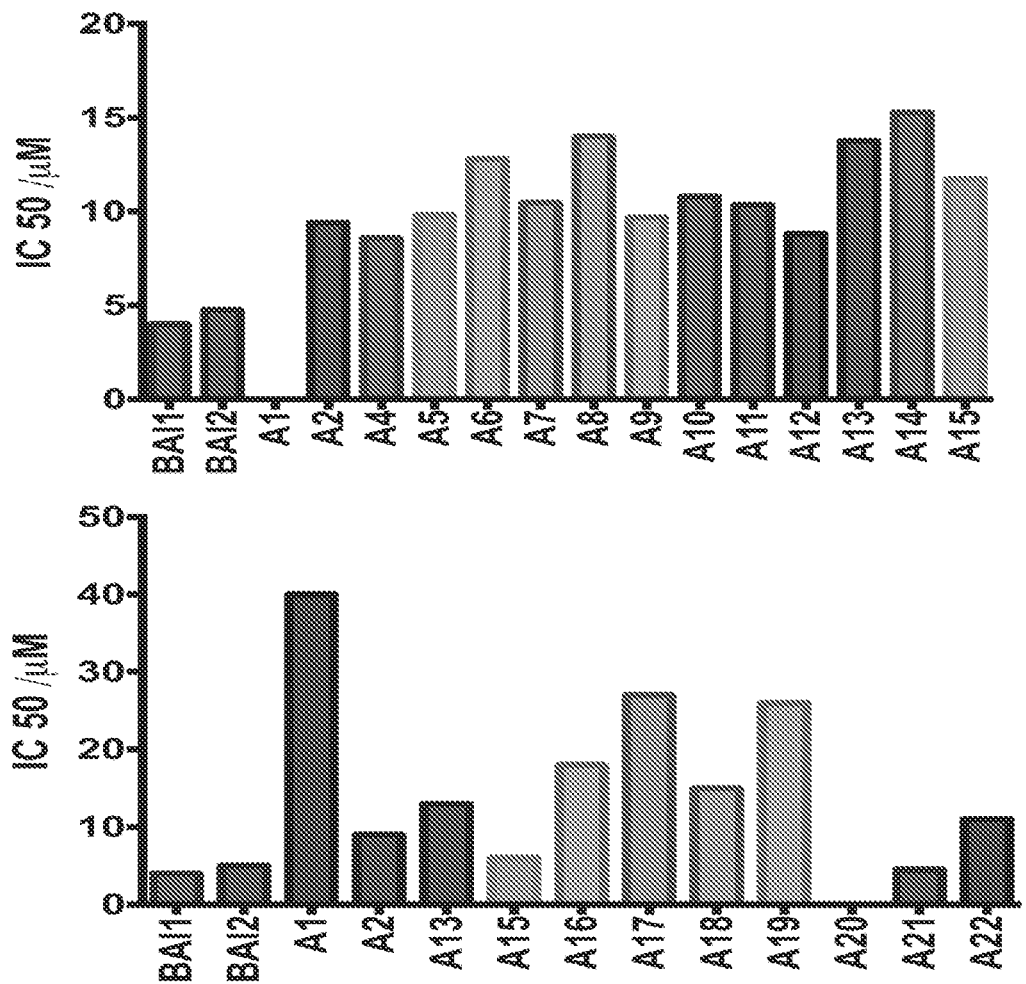
FIG. 8. BAI compounds tested in BAX inhibition assay using tBID-induced BAX activation in liposomal membranes. Structures of the compounds are shown in FIG. 3.

FIG. 8 and Table 1 show IC50 values for BAI compounds tested in a BAX inhibition assay using tBID-induced BAX activation in liposomal membranes. The structures of the compounds are shown in FIG. 3.

Figure 9:
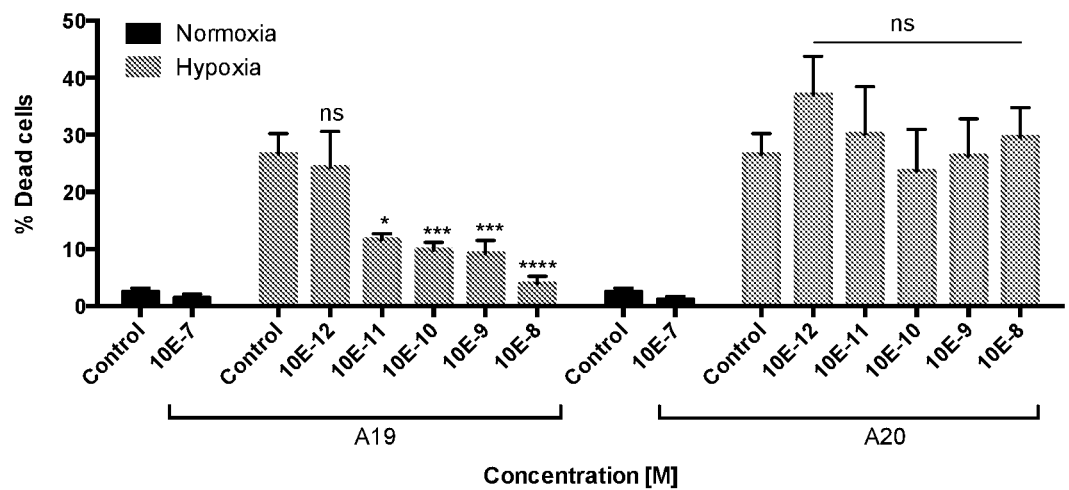
FIG. 9. BAI-A19 potently inhibits primary neonatal cardiomyocyte death induced by hypoxia, whereas the inactive analog, BAI1-A20, does not. Cell death was assessed using calcein AM (alive) and ethidium homodimer (dead) staining.

FIG. 9 shows that BAI-A19 potently inhibits primary neonatal cardiomyocyte death induced by hypoxia, whereas the inactive analog, BAI-A20, does not.

Figure 10:
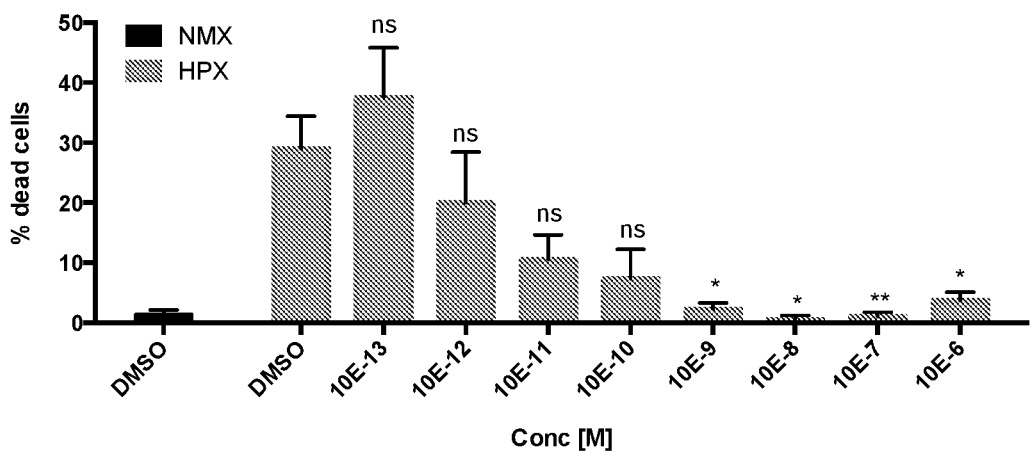
FIG. 10. BAI-A22 potently inhibits primary neonatal cardiomyocyte death induced by hypoxia.
Figure 11A:
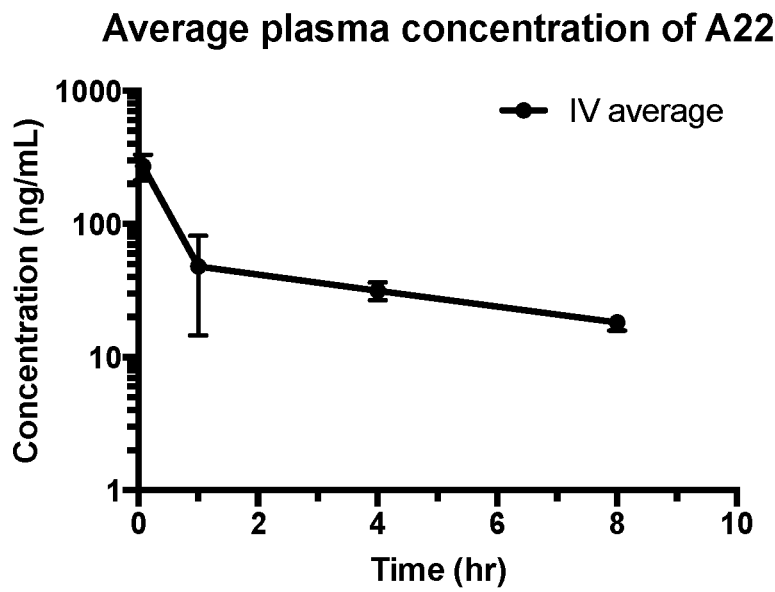
FIG. 11A-11B. BAI-A22 pharmacokinetics. BAI-A22 was injected intravenously in male Sprague Dawley® rats at 1 mg/kg dose and blood plasma and heart tissue were collected at different time points, and drug levels measured by LC-MS/MS. (A) Average BAI-A22 concentrations in blood plasma. (B) Average BAI-A22 concentrations in heart tissue.
Figure 11B:
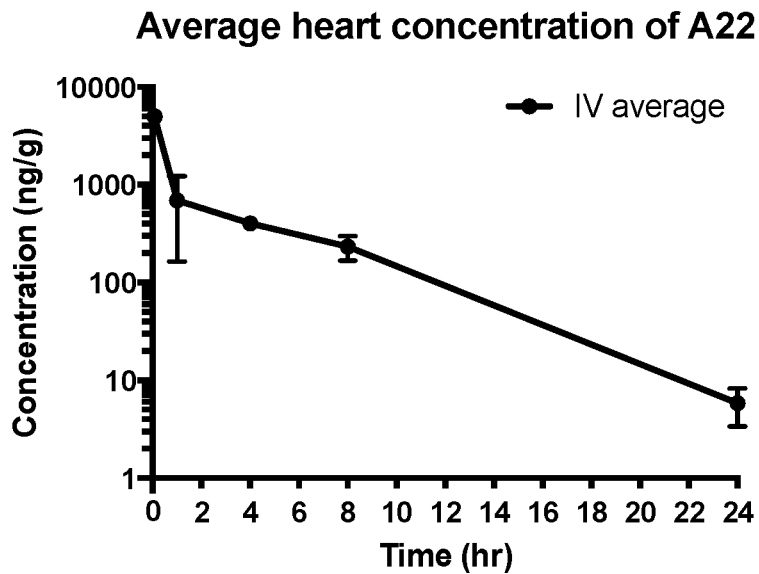
Figure 12:
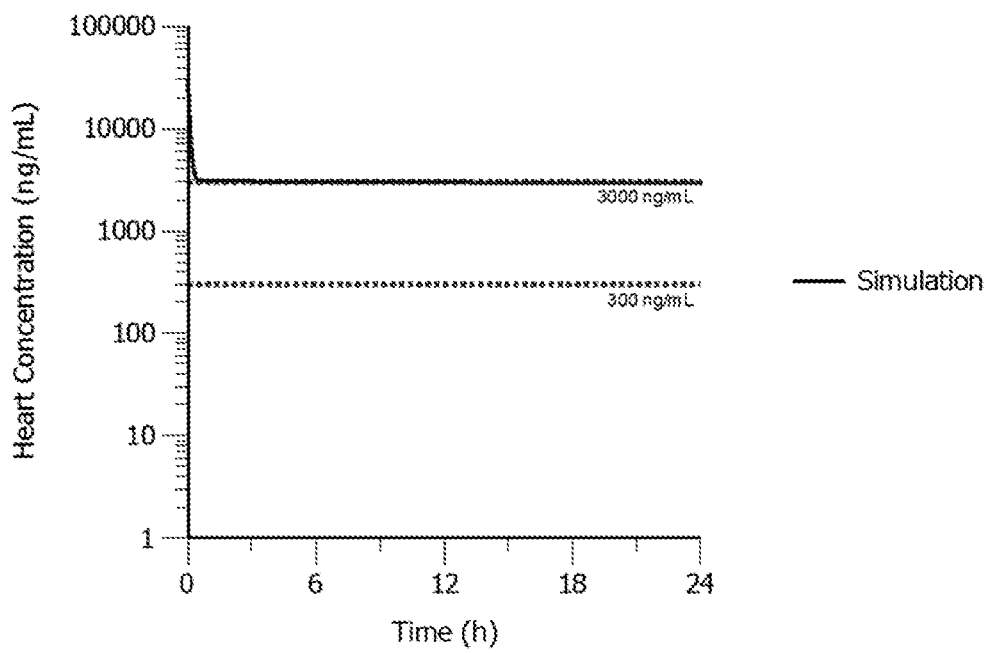
FIG. 12. Simulated heart concentration of BAI-A22. Dose Regimen to reach 3000 µg/mL heart concentration: 650 µg of IV bolus and 132 µg/h IV infusion. Dotted lines indicate the therapeutic window.
Figure 18:
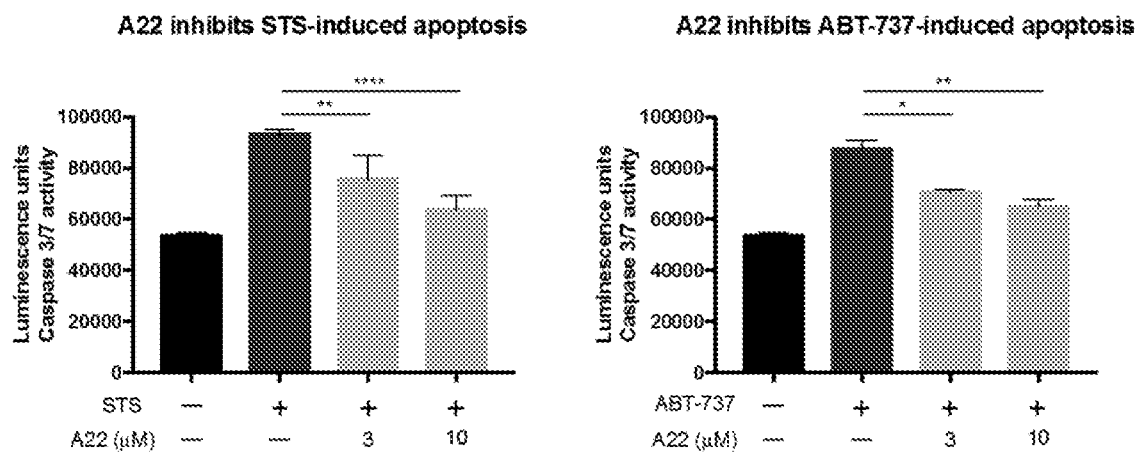
FIG. 18. BAI-A22 inhibits doxorubicin-induced apoptosis in mouse embryonic fibroblasts. Apoptosis was induced with either staurosporine (STS) or pro-apoptotic ABT-737 drug.

FIG. 18 shows that BAI-A22 inhibits doxorubicin-induced apoptosis in mouse embryonic fibroblasts. FIG. 10 shows that BAI-A22 potently inhibits primary neonatal cardiomyocyte death induced by hypoxia. FIG. 11 shows BAI-A22 pharmacokinetics in blood plasma and heart tissue. Pharmacokinetic parameters for BAI-A22 are shown in Table 2. Plasma protein binding was measured in rats for BAI-A22, which was found to be 95.6% bound. FIG. 12 shows the simulated heart concentration of BAI-A22.

Figure 21A:
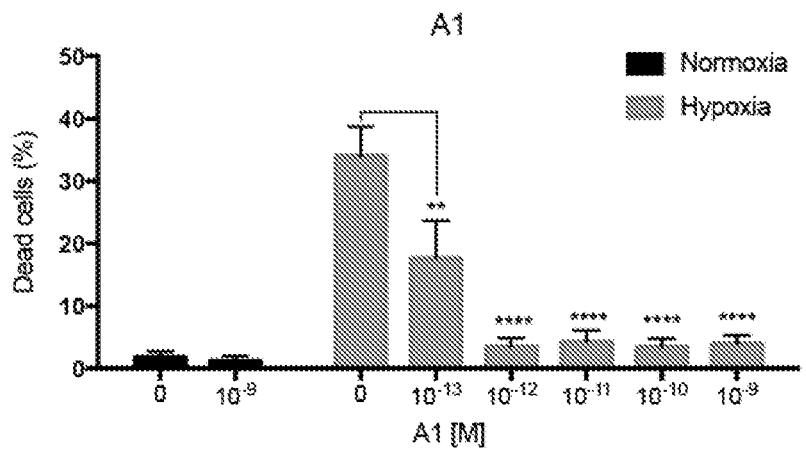
FIG. 21A-21C. BAI-A1, BAI-A2 and BAI-A21 inhibit cardiomyocyte necrotic cell death. NRCM were pre-treated with varying concentrations of BAI-A1 (A), BAI-A2 (B) or BAI-A21 (C) and cultured under normoxic or hypoxic conditions. Percentage of dead cells represents percentage of EthD positive cells.
Figure 21B:
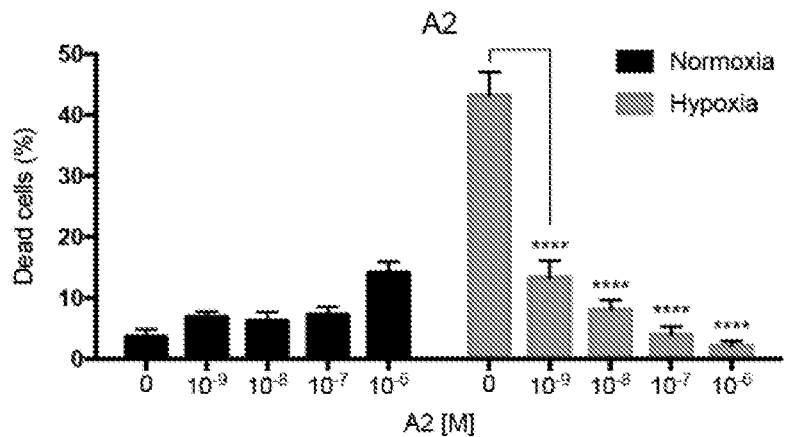
Figure 21C:
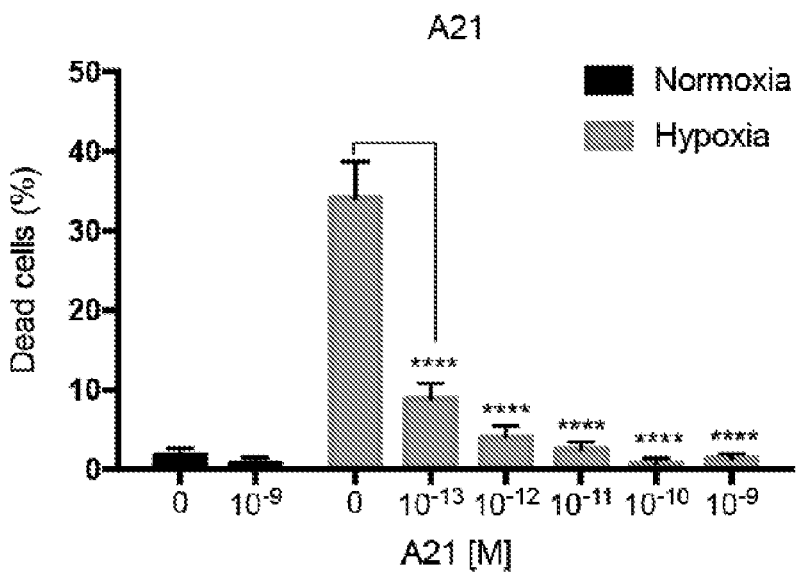
Figure 22A:
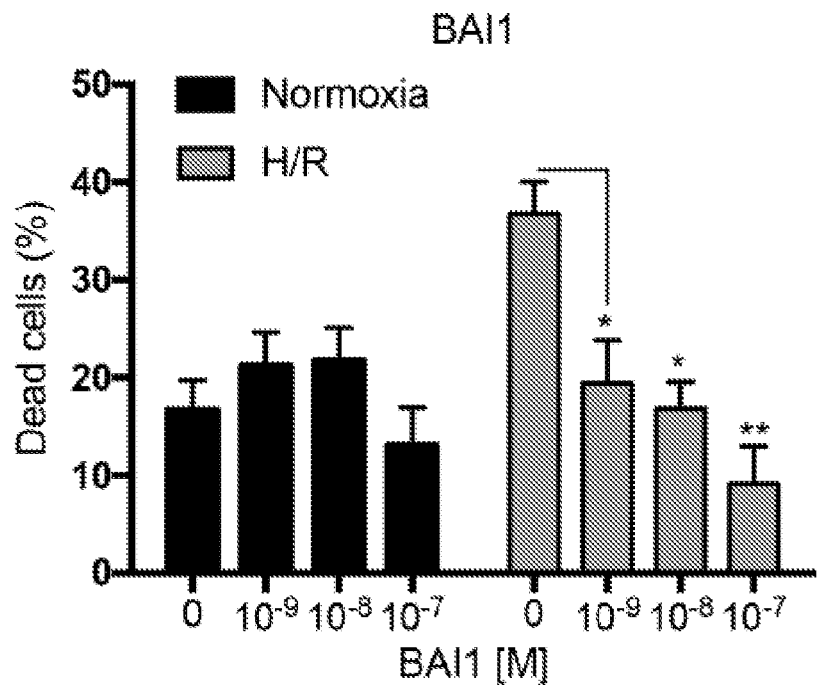
FIG. 22A-22B. BAI-1 and BAI-A1 inhibit adult cardiomyocyte necrosis. Adult rat cardiomyocytes were pre-treated with varying concentrations of BAI-1 (A) or BAI-A1 (B) and subjected to hypoxia and reoxygenation (H/R). Percentage of dead cells represents percentage of EthD positive cells.
Figure 22B:
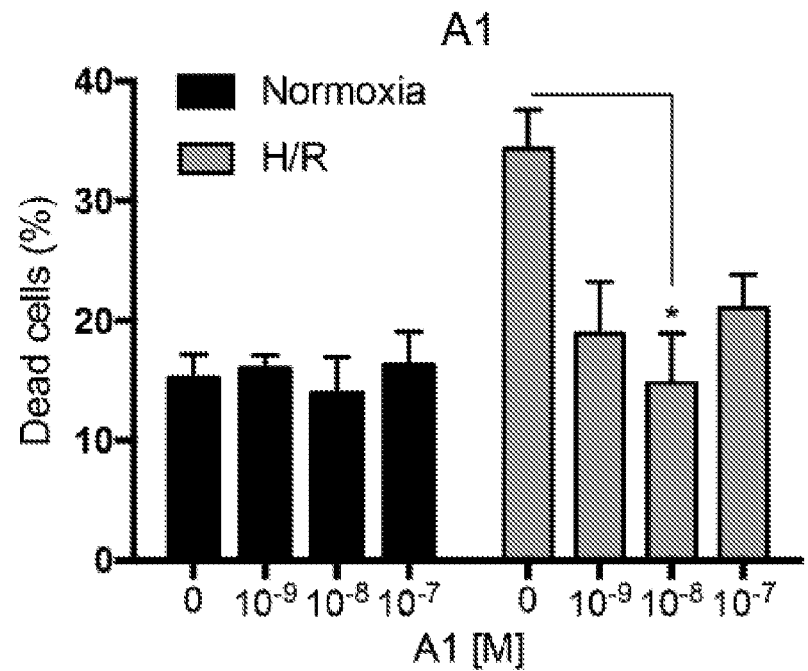

Compounds BAI-1 (FIG. 22A), BAI-A1 (FIGS. 21A, 22B), BAI-A2 (FIG. 21B) and BAI-A21 (FIG. 21C) inhibit necrosis in cardiomyocytes in a dose-dependent manner.

Pharmacokinetic properties were determined for compounds BAI-1, BAI-A1 and BAI-A22. Their half-life in plasma was, respectively, 45 hours, 3.5 hours and 5 hours.

In Vivo Studies

Effects of BAX Inhibitors on Chemotherapy-Induced Cardiotoxicity.

Doxorubicin is extensively used for both adults and children to treat many types of cancers, including solid tumors, such as breast cancer, leukemia and lymphomas (27). It is considered as one of the most potent of the Food and Drug Administration (FDA)-approved cancer drugs (28). Doxorubicin's clinical use is limited by its severe dose-dependent and often lethal heart failure (27), even emerging years after termination of treatment (29).

Studies using BAX knockout mice showed that deletion of Bax protected mice from doxorubicin-induced cardiac dysfunction as measured by improvements in fractional shortening and systolic wall thickening and decreases in apoptotic and necrotic cardiac cell death (data not shown).

Figure 19A:
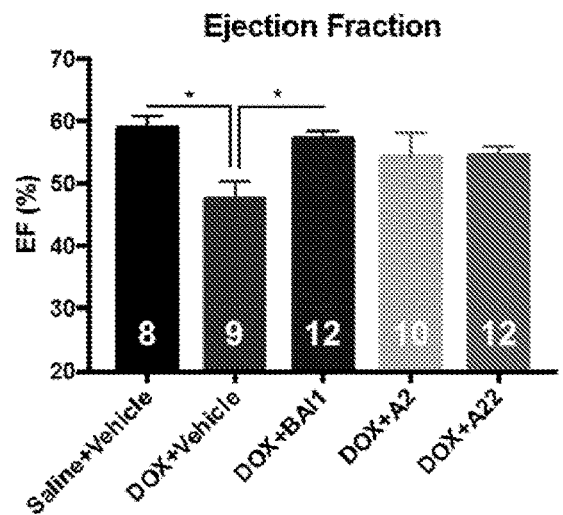
FIG. 19A-19C. BAX inhibitor effect on heart function in doxorubicin-treated mice. (A) Effects of doxorubicin with or without BAX inhibitors BAI-1, BAI-A2, and BAI-A22 on ejection fraction in acute doxorubicin model. Groups were compared using one-way ANOVA followed by Tukey's multiple comparisons test. (B) Effect of doxorubicin with or without BAX inhibitor BAI-1 on ejection fraction in acute doxorubicin model. Groups were compared using one-way ANOVA followed Dunnett's multiple comparisons test. (C) Effect of doxorubicin with or without BAX inhibitor BAI-A22 on ejection fraction in acute doxorubicin model. Groups were compared using one-way ANOVA followed Dunnett's multiple comparisons test.
Figure 19B:
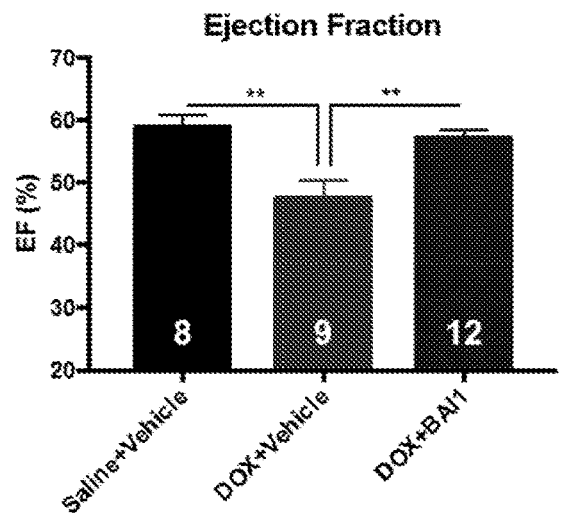
Figure 19C:
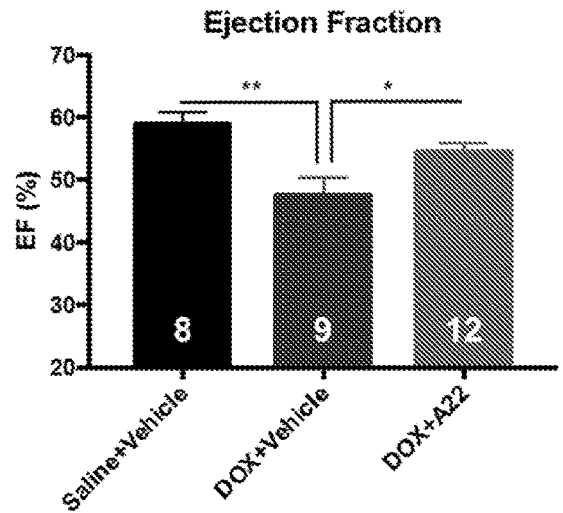

Doxorubicin-induced cardiotoxicity is known to increase BAX levels and drive apoptosis in cardiac cells and is a real clinical problem. A number of new chemotherapy drugs have the same side-effect and cardiotoxicity prevents their use at more effective doses. FIG. 19A-C illustrates the effects of three BAX inhibitors on heart function in doxorubicin-treated mice. C57BL/6 male mice 8 weeks of age were purchased from Charles River Laboratories and randomly grouped (n=8 to 13). An acute heart failure model was generated by a single intraperitoneal injection of doxorubicin (20 mg/kg) dissolved in saline. BAI-1, BAI-A2 and BAI-A22 were administered to mice by a single intraperitoneal injection of 2 mg/kg dose. Both BAI-1 (FIG. 19B) and BAI-22 (FIG. 19C) were therapeutically effective at the dose used. Similar therapeutic effects were observed with BAI-21 (data not shown).

Figure 24A:
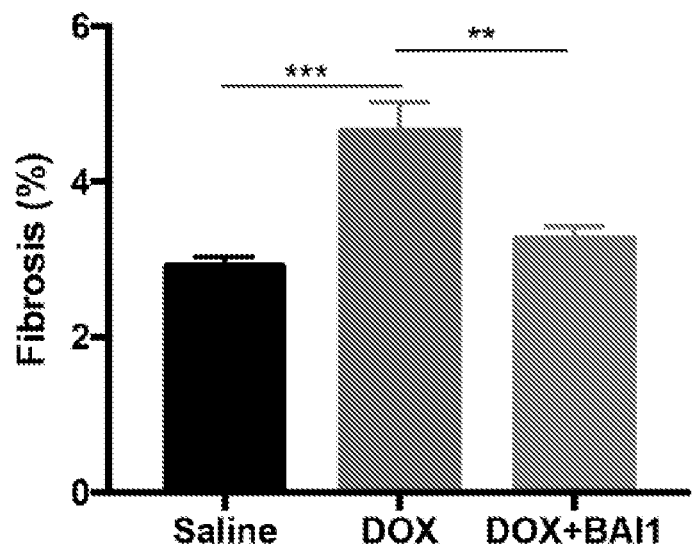
FIG. 24A-24C. BAI-1 reduces doxorubicin-induced cardiac fibrosis, apoptosis and necrosis. (A) Hearts were collected from mice in the acute doxorubicin model and sectioned to measure fibrosis using Masson Trichrome staining. Percentage of area with blue collagenous stain per field. (B) Hearts were collected from mice in the acute doxorubicin model and sectioned to stain for apoptosis marker, TUNEL. Percentage of TUNEL positive nuclei per field. (C) Hearts were collected from mice in the acute doxorubicin model and sectioned to immunostain for high motility group box 1 (HMGB1), loss of which indicates necrosis. Percentage of nuclei that lost HMGB1 per field.
Figure 24B:
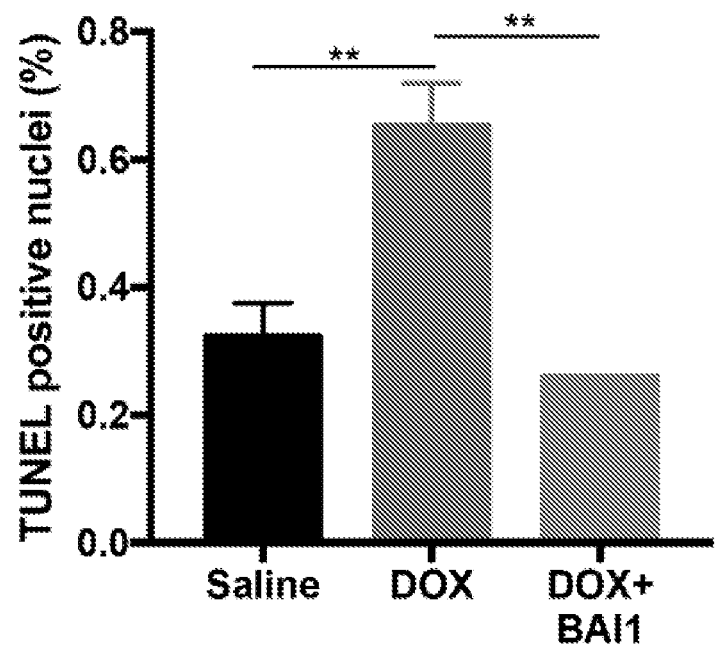
Figure 24C:
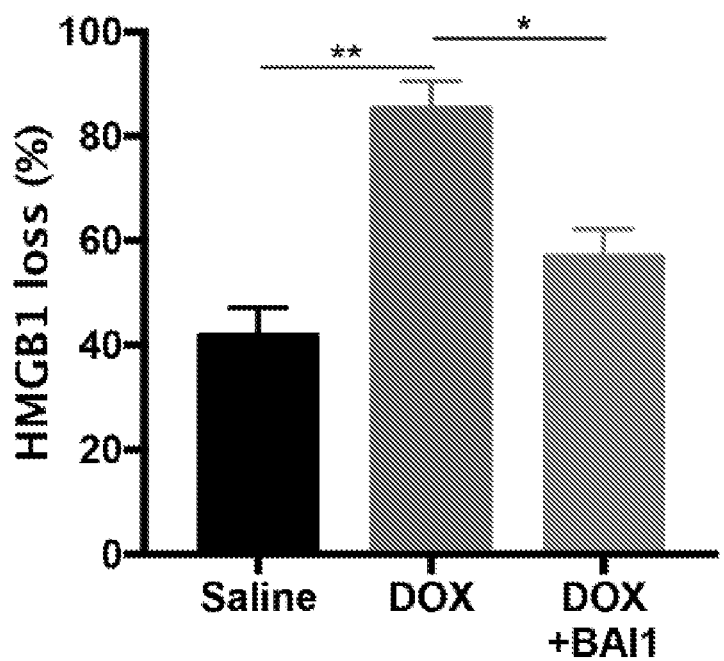

Hearts were collected from mice in the acute doxorubicin model and sectioned to measure fibrosis using Masson Trichrome staining, or stained for the apoptosis marker, TUNEL, or immunostained for HMGB1, loss of which indicates necrosis. BAI-1 reduced doxorubicin-induced cardiac fibrosis, apoptosis and cardiac necrosis (FIG. 24A-C).

Chronic Doxorubicin-Induced Cardiomyopathy Mouse Model

Patients typically receive several "cycles" of doxorubicin administered at lower doses. The exact protocol depends on the cancer being treated. For example, some leukemias are treated with 4 cycles of 60 mg/m$^2$ (which would be the equivalent of 1.5 mg/kg) IV administered every 21-28 days. Cumulative doxorubicin dose of 20-25 mg/kg has been shown to induce a clinically relevant cardiomyopathy in mice (30-32). Based on this experience, a chronic protocol was used in which mice receive 3 mg/kg doxorubicin IP every other day×8 doses (i.e. over a two-week period) for a cumulative dose of 24 mg/kg.

Figure 25A:
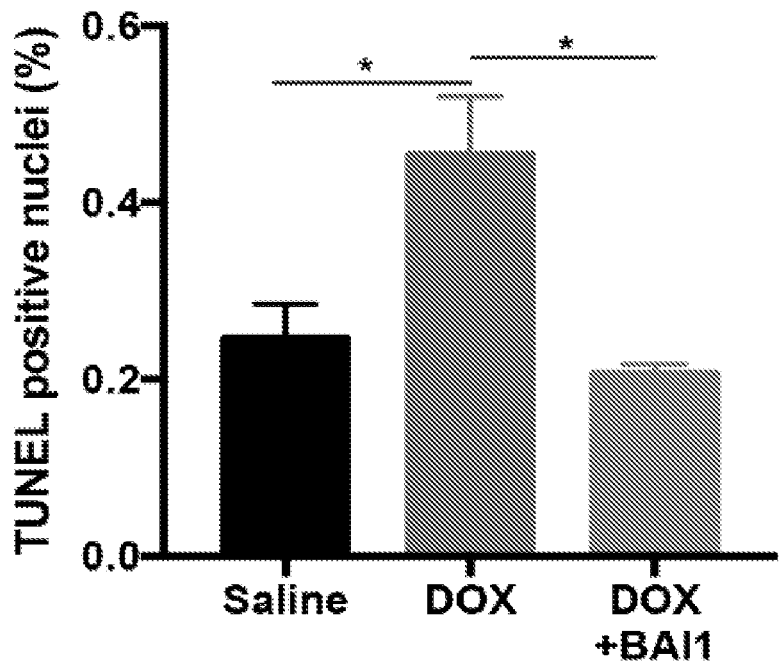
FIG. 25A-25B. BAI-1 effects on doxorubicin-induced cardiac apoptosis in chronic model. (A) Hearts were collected from mice in the chronic doxorubicin model and sectioned to stain for the apoptosis marker, TUNEL. Percentage of TUNEL positive nuclei per field. (B) Hearts were collected from mice in the chronic doxorubicin model and sectioned to immunostain for HMGB1, loss of which indicates necrosis. Percentage of nuclei that lost HMGB1 per field.
Figure 25B:
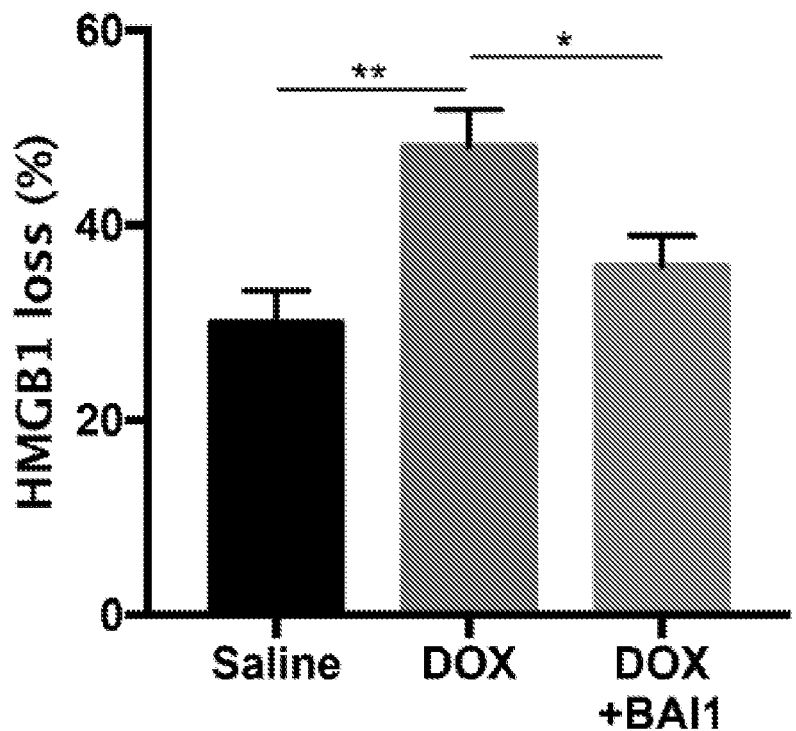

BAI-1 and BAI-A22 were tested for their ability to protect the heart against doxorubicin-induced cardiomyopathy, using a dose of 2 mg/kg. BAI1 and A22 significantly protected the heart from cardiac dysfunction as assessed by fractional shortening, ejection fraction and systolic wall thickening. Doxorubicin-induced apoptotic and necrotic cardiac cell death were largely abrogated as tested using BAI-1, as shown by TUNEL (FIG. 25A) and HMGB1 loss (FIG. 25B), respectively.

Figure 26:
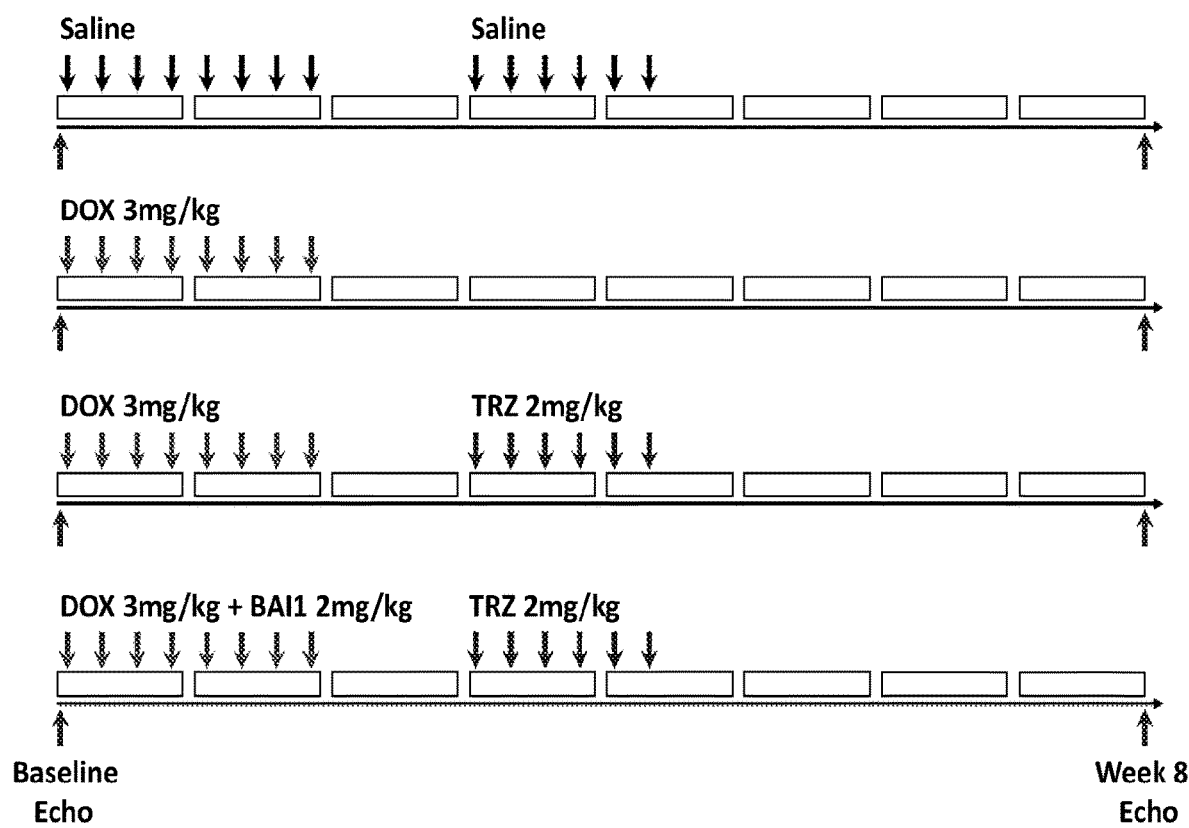
FIG. 26. Chronic model of doxorubicin and trastuzumab combination therapy. Experimental scheme for chronic model of doxorubicin and trastuzumab-induced cardiomyopathy. In doxorubicin group, mice were administered 3 mg/kg doxorubicin for 8 injections. In doxorubicin plus trastuzumab group, mice were administered 1 week later with 2 mg/kg trastuzumab for 6 injections. Echocardiography was performed at week 8 from the start of experiment. Trastuzumab (TRZ).
Figure 27:
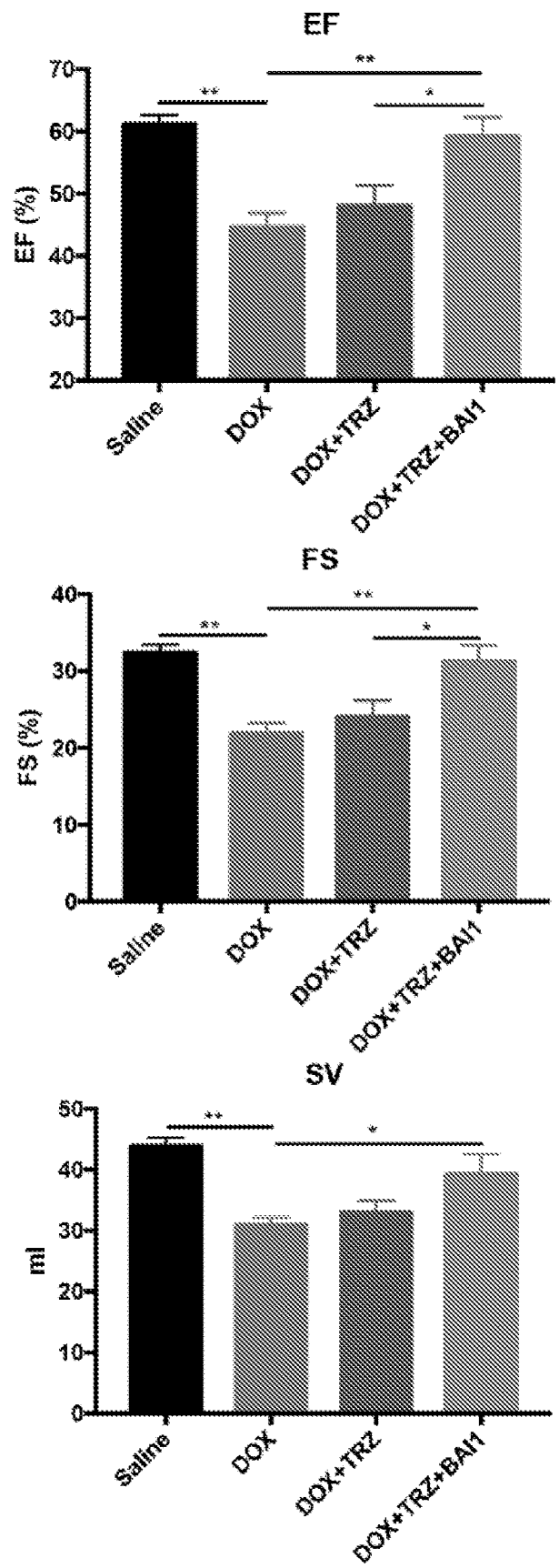
FIG. 27. BAI-1 protects the heart against doxorubicin and trastuzumab combination therapy. Echocardiographic assessment of cardiac function and dimensions showing significant rescue by BAI-1. Ejection fraction (EF); fractional shortening (FS); stroke volume (SV). Trastuzumab (TRZ). Saline, n=6; DOX, n=8; DOX+TRZ, n=8; DOX+TRZ+BAI1, n=8 mice.

Trastuzumab is a humanized monoclonal antibody against the human epidermal growth factor receptor 2 (HER2) receptor and was approved by the FDA in 1998 as a therapy for HER2-positive breast cancer patients (33, 34). The combination of doxorubicin with tratuzumab increases treatment efficacy but also is often accompanied by increased cardiotoxicity (35). The effects of BAI-1 were tested using the chronic doxorubicin model followed by the initiation one week later of trastuzumab (FIG. 26). Echocardiography was performed at week 8 following initiation of doxorubicin. Results show that doxorubicin+trastuzumab induced cardiac dysfunction was inhibited by BAI-1 as assessed using ejection fraction, fractional shortening and stroke volume (FIG. 27).

BAI-1 does not Inhibit Doxorubicin-Induced Cancer Cell Death

Figure 28:
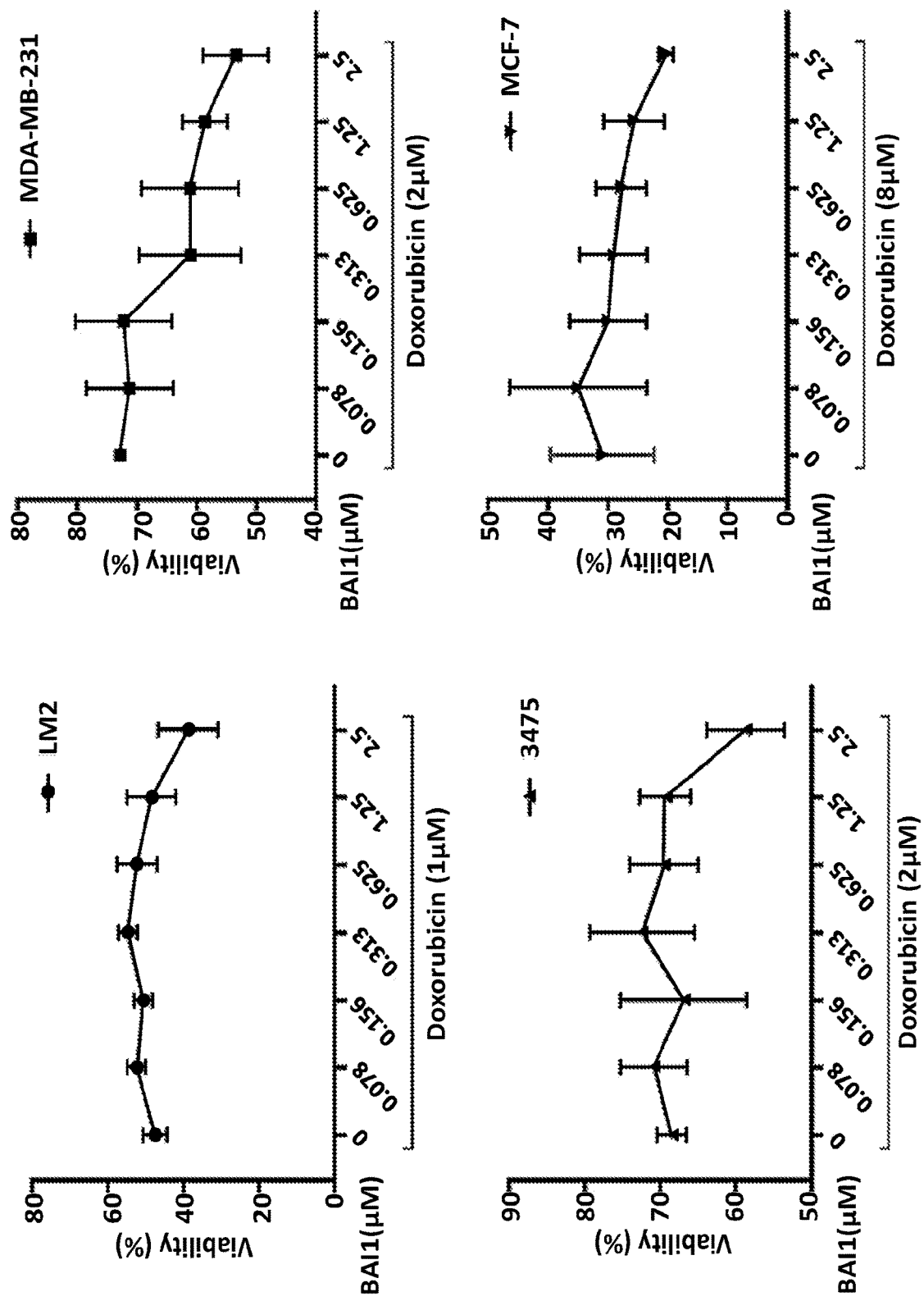
FIG. 28. BAI-1 does not inhibit doxorubicin-induced breast cancer cell death. Human breast cancer cell lines LM2, MDA-MB-231, 3475 and MCF-7 were treated with doxorubicin without or with varying concentrations of BAI-1. Percentage of cell viability is relative to 100% viability of an untreated control group (not shown). BAI-1 did not interfere with doxorubicin-induced killing of any of the breast cancer cells. Cell viability was assessed using CytoTox-Glo Cytotoxicity Assay (Promega).

FIG. 28 illustrates human breast cancer cell lines LM2, MDA-MB-231, 3475 and MCF-7 treated with doxorubicin without or with varying concentrations of BAI-1. BAI-1 did not interfere with doxorubicin-induced killing of any of the breast cancer cells. Co-treatment with BAI-1 also did not compromise the cytotoxic effect of doxorubicin in an in vivo breast cancer xenograft mouse model (data not shown).

Figure 29:
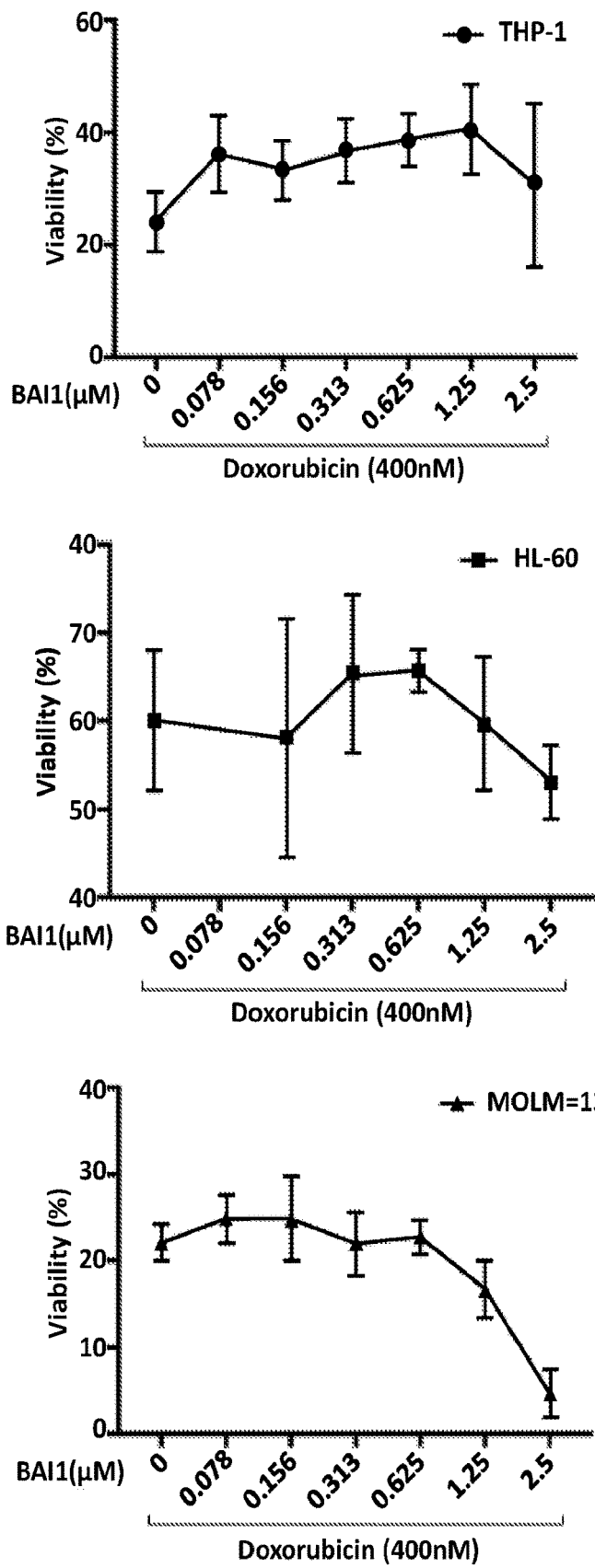
FIG. 29. Effects of BAI-1 on doxorubicin-induced AML cell viability in vitro. Human AML cell lines THP-1, HL-60 and MOLM-13 were treated with doxorubicin without or with varying concentrations of BAI-1. Percentage of cell viability is relative to 100% viability of an untreated control group (not shown). BAI-1 did not interfere with doxorubicin-induced killing of any of the AML cells.

BAI-1 also did not effect of the ability of doxorubicin to kill acute myeloid leukemia (AML) cell lines in culture (FIG. 29). Co-treatment with BAI-1 also did not compromise the cytotoxic effect of doxorubicin in an in vivo AML heterograft mouse model (data not shown). BAI-1 protected against doxorubicin-induced cardiomyopathy in the same mice whose leukemia burden was successfully reduced by doxorubicin. These results indicate that BAI-1 can protect against doxorubicin-induced cardiomyopathy without interfering with reduction of leukemia burden in the same animals.

BAX levels were assessed in the adult heart versus the 4 breast cancer and 3 AML cell lines that were studied above. BAX levels were uniformly increased in the cancer cell lines compared with the heart. Next, to test the functional significance of the high BAX levels in tumor cells as a mechanism to escape BAI-1 from inhibiting doxorubicin-induced killing, BAX levels were knocked down in THP-1 AML cells using siRNA. While 73% reduction in BAX levels did not affect basal killing by doxorubicin, it resulted in BAI-1 interfering with doxorubicin-induced apoptosis (data not shwon). These data suggest that high BAX levels in tumors compared to the heart may be one mechanism by which BAI-1 protects the heart against doxorubicin without interfering with its killing of tumor cells.

TABLE 1

BAX inhibition activity of BAI compounds in liposomal assays upon tBID-induced BAX activation.

| Inhibitor | Predicted IC50/μM | Measured IC 50/μM |
|---|---|---|
| BAI1 | 4.0 | 4.0 |
| BAI2 | 4.8 | 5.0 |
| BAI-A1 | >20 | 40.0 |
| BAI-A2 | 9.4 | 9.0 |
| BAI-A4 | 8.6 | — |
| BAI-A5 | 9.8 | — |
| BAI-A6 | 12.8 | — |
| BAI-A7 | 10.5 | — |
| BAI-A8 | 14.0 | — |

TABLE 1-continued

BAX inhibition activity of BAI compounds in liposomal assays upon tBID-induced BAX activation.

| Inhibitor | Predicted IC50/μM | Measured IC 50/μM |
|---|---|---|
| BAI-A9 | 9.7 | — |
| BAI-A10 | 10.8 | — |
| BAI-A11 | 10.4 | — |
| BAI-A12 | 8.8 | — |
| BAI-A13 | 13.8 | 13.0 |
| BAI-A14 | 15.3 | — |
| BAI-A15 | 11.7 | 6.0 |
| BAI-A16 | — | 18.0 |
| BAI-A17 | — | 27.0 |
| BAI-A18 | — | 15.0 |
| BAI-A19 | — | 26.0 |
| BAI-A20 | — | >>100 |
| BAI-A21 | — | 4.5 |
| BAI-A22 | — | 11 |

IC50 values were measured using liposome release experiments using a minimum of 4 inhibitor concentrations around the IC50. Normalized inhibition values are the percentage inhibition of each compound normalized to BAI1, averaged over 5 and 10 μM inhibitor concentrations. IC50 were predicted based on of "Normalized inhibition values" correlated with measured IC50 values.

TABLE 2

BAI-A22 pharmacokinetic parameter estimates from NCA

| Parameter | Units | Estimate |
|---|---|---|
| $t_{1/2}$ | hr | 5.04 |
| $t_{max}$ | hr | 0 |
| $C_{max}$ | ng/mL | 318 |
| $C_0$ | ng/mL | 318 |
| $MRT_{last}$ | hr | 2.15 |
| CL | L/hr/kg | 1.91 |
| $V_{ss}$ | L/kg | 10.5 |
| $AUC_{last}$ ± SE | hr*ng/mL | 390 ± 42.7 |
| $AUC_\infty$ | hr*ng/mL | 524 |

Pharmacokinetic parameters from non-compartmental analysis using WinNonLin software. $C_0$: maximum plasma concentration extrapolated to t=0; $t_{max}$: time of maximum plasma concentration; $t_{1/2}$: half-life; $MRT_{last}$: mean residence time, calculated to the last observable time point; CL: clearance; $V_{ss}$: steady state volume of distribution; $AUC_{last}$: area under the curve, calculated to the last observable time point; $AUC_\infty$: area under the curve, extrapolated to infinity.

Materials and Methods for the Chemical Syntheses

All chemical reagents and solvents were obtained from commercial sources (Aldrich, Acros, Fisher) and used without further purification unless otherwise noted. Anhydrous solvents (tetrahydrofurane, toluene, dichloromethane, diethyl ether) were obtained using a Pure Solv™ AL-258 solvent purification system. N,N-Dimethylformamide was degassed and dried over freshly activated 4 Å molecular sieves. Chromatography was performed on a Teledyne ISCO CombiFlash Rf 200i using disposable silica cartridges (4, 12, and 24 g). Analytical thin layer chromatography (TLC) was performed on aluminum-backed Silicycle silica gel plates (250 μm film thickness, indicator F254). Compounds were visualized using a dual wave length (254 and 365 nm) UV lamp, and/or staining with CAM (cerium ammonium molybdate) or $KMnO_4$ stains. NMR spectra were recorded on Bruker DRX 300 and DRX 600 spectrometers. $^1$H and $^{13}$C chemical shifts (δ) are reported relative to tetramethyl silane (TMS, 0.00/0.00 ppm) as internal standard or to residual solvent (CD3OD: 3.31/49.00 ppm; $CDCl_3$: 7.26/77.16 ppm; dmso-$d_6$: 2.50/39.52 ppm; acetone-$d_6$: 2.05/29.84 ppm; acetonitrile-$d_3$: 1.94/1.32 ppm). Mass spectra were recorded on a Shimadzu LCMS 2010EV (direct injection unless otherwise noted).

3,6-difluoro-9H-carbazole (22), 3,6-bis(trifluoromethyl)-9H-carbazole (23), 3,6-dimethyl-9H-carbazole (24), and tert-butyl piperazine-1-carboxylate (25) were synthesized according to literature procedures. As an alternative to Pd-catalyzed aminations, requisite diaryl amnines can be conveniently prepared using Knochel's procedure (26).
Typical Synthetic Procedure—Synthesis of BAI-A22

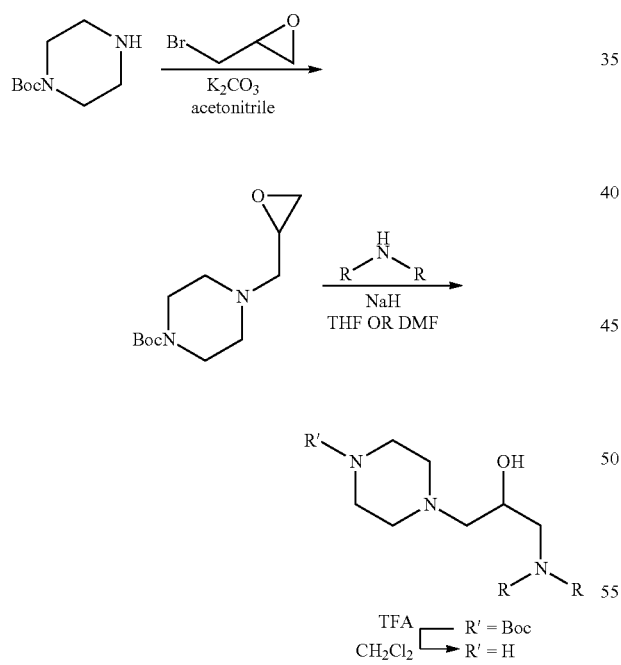

Scheme 1: Synthesis of BAI-A22 and its analogs. tert-Butyl piperazine-1-carboxylate was added to 2-(bromomethyl) oxirane to give intermediate. Amines were deprotonated using sodium hydride and used to open the epoxide. The resulting secondary alcohol was subjected to standard Boc deprotection conditions to obtain BAI-A22 and its analogs. (THF=tetrahydrofurane; DMF=N,N-dimethylformamide, TFA=trifluoroacetic acid; Boc=tert-butylcarboxylate)

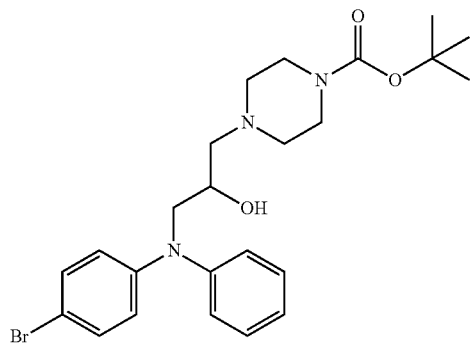 [SMILES: CC(C)(C)OC(=O)N1CCN(CC(O)CN(c2ccccc2)c2ccc(Br)cc2)CC1]

Synthesis of tent-butyl 4-(3-((4-bromophenyl)(phenyl) amino)-2-hydroxypropyl)piperazine-1-carboxylate. In a flame-dried 60 mL Centrifuge tube with septum and stir bar, sodium hydride (60% dispersion in mineral oil) (258 mg, 6.45 mmol, 1.60 equiv) was suspended in dry DMF (5.7 mL) under an argon atmosphere. In a separate dry and argon-flushed tube, 4-bromo-N-phenylaniline (1.50 g, 6.05 mmol, 1.50 equiv) was dissolved in dry DMF (18.4 mL). The NaH-suspension was cooled to 0° C. (ice bath) and the diphenylamine solution was slowly added over ca 10-15 min. A color change to bright yellow, later green was observed. After 20 min, the mixture was warmed to room temperatue (RT) and stirred for an additional 30 min. The mixture then was cooled to 0° C. again.

A solution of tert-butyl 4-(oxiran-2-ylmethyl)piperazine-1-carboxylate (0.977 g, 4.03 mmol) in dry DMF (2.83 mL) was added over 5 min. The mixture was stirred at 0° C. for 10 min, then warmed to RT and stirred at this temperature. Thin layer chromatography (TLC; 1:1 hex:EtOAc) was used to monitor the reaction progress. After TLC indicated full conversion, the mixture was poured onto satd. aq. sodium bicarbonate (75.0 mL), extracted with EtOAc (150 mL and 2×75.0 mL). Combined organic layers were dried ($MgSO_4$), filtered and evaporated in vacuo. The crude residue was purified on an Isco CombiFlash (silica gel, EtOAc in hexanes, 30%→60%) (BAI-A22; 605 mg, 1.23 mmol, 31%) was obtained as off-white solid. The corresponding O-acetate (1.01 g) was isolated as a side-product. The acetate had presumably formed on the loading column from the desired product and ethyl acetate, triggered by heat formed when DMF remainders in the crude material came in contact with the silica. This behavior was not observed on a significant level in smaller scale reactions and can be avoided by more thorough drying of the crude in high vacuum ($10^{-3}$ mbar). The acetate can be conveniently hydrolyzed by treatment with potassium carbonate (2.0 equiv) in methanol (0.11 M) for 2 h to give another crop of the desired product (685 mg, 35%).

TLC: $R_f$ 0.37 (1:1, hex:EtOAc). $^1$H-NMR (600 MHz, $CDCl_3$): δ 7.32-7.28 (m, 4H), 7.08 (d, J=7.9 Hz, 2H), 7.03 (t, J=7.4 Hz, 1H), 6.88 (d, J=8.9 Hz, 2H), 4.00 (dd, J=10.3, 5.7 Hz, 1H), 3.79-3.71 (m, 2H), 3.44-3.38 (m, 4H), 3.31 (s, 1H), 2.53-2.52 (m, 2H), 2.41 (dd, J=12.4, 3.5 Hz, 1H), 2.34 (m, 3H), 1.45 (s, 9H). $^{13}$C-NMR (151 MHz, $CDCl_3$): δ 154.8, 147.9, 147.8, 132.2, 129.7, 122.9, 122.7, 121.6, 113.2, 80.0, 65.1, 62.27, 56.8, 53.2, 43.8 (d, br), 28.6. ESI-MS m/z (rel int): (pos) 514.1 ([M($^{81}$Br)+Na]$^+$, 18), 512.1 ([M($^{79}$Br)+Na]$^+$, 14), 492.1 ([M($^{81}$Br)+H]$^+$, 100), 490.1 ([M($^{79}$Br)+H]$^+$, 95), 436.0 (14), 435.0 (18).

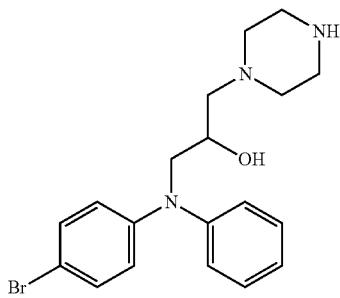

BAI-A22

Synthesis of 1-((4-bromophenyl)(phenyl)amino)-3-(piperazin-1-yl)propan-2-ol (BAI-A22). tert-Butyl 4-(3-((4-bromophenyl)(phenyl)amino)-2-hydroxypropyl)piperazine-1-carboxylate (605 mg, 1.23 mmol) was dissolved in dichloromethane (20.6 mL). The flask was purged with argon for a few minutes, and TFA (5.23 mL, 67.8 mmol, 55.0 equiv) was added at RT and the mixture stirred at the same temperature. TLC analysis of a reaction aliquot (microworkup, satd. aq. NaHCO3/EtOAc) indicated complete conversion after 1 h 05'. The mixture was poured on sodium bicarbonate (6.22 g, 74.0 mmol, 60.0 equiv) in 20.0 mL water and stirred vigorously at RT for 40 min. More sodium bicarbonate was added as needed to bring the aqueous layer to pH=8. The layers were separated and the aqueous layer was extracted with EtOAc (2×75.0 mL). The combined organic layers were washed with satd. aq. NaHCO$_3$ (50.0 mL) and brine (50.0 mL), dried (MgSO4), filtered and evaporated in vacuo. The residue was taken up in CH$_2$Cl$_2$, filtered through syringe filter (pore size), then evaporated in vacuo and dried in high vacuum (foams heavily!). Ethyl-3-oxo-3-phenyl-2-(2-(thiazol-2-yl)hydrazono)propanoate (470 mg, 1.20 mmol, 98%) was obtained as a sticky, light brown solid.

TLC: R$_f$ 0.09 (95:5, CH$_2$Cl$_2$:MeOH). $^1$H-NMR (600 MHz, CDCl$_3$): δ 7.33-7.28 (m, 4H), 7.09 (dd, J=8.6, 1.1 Hz, 2H), 7.03 (tt, J=7.3, 1.1 Hz, 1H), 6.89 (d, J=9.0 Hz, 2H), 4.03-3.98 (m, 1H), 3.78-3.70 (m, J=5.7 Hz, 2H), 2.94-2.87 (m, 4H), 2.63-2.60 (m, 2H), 2.44-2.38 (m, 3H), 2.30 (dd, J=12.4, 10.1 Hz, 1H). $^{13}$C-NMR (151 MHz, CDCl$_3$): δ 147.9, 147.8, 132.2, 129.7, 122.9, 122.7, 121.6, 113.2, 64.8, 62.7, 56.9, 54.2, 46.0. ESI-MS m/z (rel int): (pos) 392.09 ([M($^{81}$Br)+H]$^+$, 100), 389.9 ([M($^{79}$Br)+H]$^+$, 99).

Final products can be converted into their (e.g., HCl) salts.

Synthesis of Additional Compounds

The following compounds were prepared in an analogous fashion.

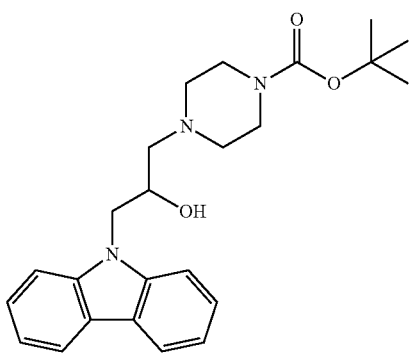 [SMILES: CC(C)(C)OC(=O)N1CCN(CC(O)Cn2c3ccccc3c3ccccc32)CC1]

TLC: R$_f$ 0.20 (1:1, hex:EtOAc). $^1$H-NMR (600 MHz, CDCl$_3$): δ 8.10 (dt, J=7.7, 0.9 Hz, 2H), 7.50-7.46 (m, 4H), 7.26 (ddd, J=7.7, 6.0, 1.8 Hz, 3H), 4.40 (d, J=5.4 Hz, 2H), 4.28 (m, J=5.3 Hz, 1H), 3.45-3.36 (m, J=3.3 Hz, 4H), 2.54-2.45 (m, 4H), 2.32 (s, 2H), 1.44 (s, 9H). $^{13}$C-NMR (151 MHz, CDCl$_3$): δ 154.8, 141.1, 125.9, 123.2, 120.4, 119.3, 109.2, 80.0, 66.5, 62.0, 53.1, 47.2, 43.7 (d, br), 28.5. ESI-MS m/z (rel int): (pos) 432.1 ([M+Na]$^+$, 100); (neg) 444.2 ([M+Cl]$^-$, 100).

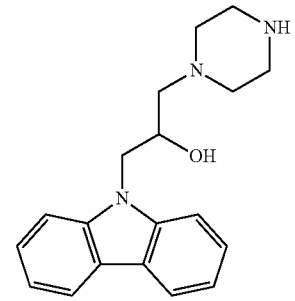

BAI-A1

TLC: R$_f$ 0.24 (95:5, CH$_2$Cl$_2$:MeOH). $^1$H-NMR (600 MHz, dmso-d$_6$): δ 8.13 (d, J=7.7 Hz, 2H), 7.63 (d, J=8.2 Hz, 2H), 7.43 (t, J=7.7 Hz, 2H), 7.18 (t, J=7.4 Hz, 2H), 4.99-4.91 (m, 1H), 4.48-4.45 (m, 1H), 4.29 (dd, J=14.8, 6.9 Hz, 1H), 4.10-4.03 (m, 1H), 2.86-2.80 (m, 4H), 2.44-2.32 (m, 6H). $^{13}$C-NMR (151 MHz, dmso-d$_6$): δ 131.0, 115.7, 112.4, 110.3, 108.9, 100.2, 57.36, 52.5, 43.3, 37.9, 34.8. ESI-MS m/z (rel int): (pos) 310.0 ([M+H]$^+$, 100).

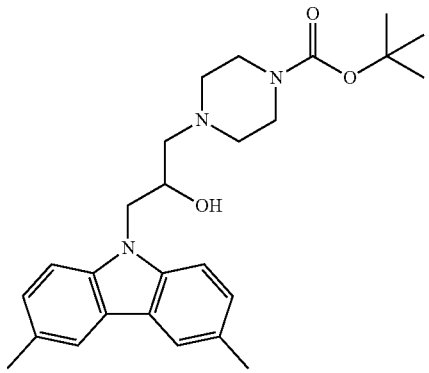 [SMILES: Cc1ccc2c(c1)c1cc(C)ccc1n2CC(O)CN1CCN(C(=O)OC(C)(C)C)CC1]

TLC: R$_f$ 0.29 (1:1, hex:EtOAc). $^1$H-NMR (600 MHz, CDCl$_3$): δ 7.84 (s, 2H), 7.33 (d, J=7.1 Hz, 2H), 7.26 (d, J=7.1 Hz, 2H), 4.37-4.31 (m, 2H), 4.22-4.22 (br s, 1H), 3.39 (br s, 4H), 2.52-2.41 (m, 11H), 2.29 (br s, 2H). $^{13}$C-NMR (151 MHz, CDCl$_3$): δ 154.8, 139.7, 128.4, 127.0, 123.1, 120.4, 108.8, 80.0, 66.5, 62.0, 53.1, 47.2 (br d), 43.6, 28.5, 21.5. ESI-MS m/z (rel int): (pos) 460.2 ([M+Na]⁺, 34), 438.1 ([M+H]⁺, 100); (neg) 472.3 ([M+Cl]⁻, 45), 436.4 ([M−H]⁻, 10).

br), 28.5. ESI-MS m/z (rel int): (pos) 446.0 ([M+H]⁺, 100); (neg) 480.1 ([M+Cl]⁻, 100).

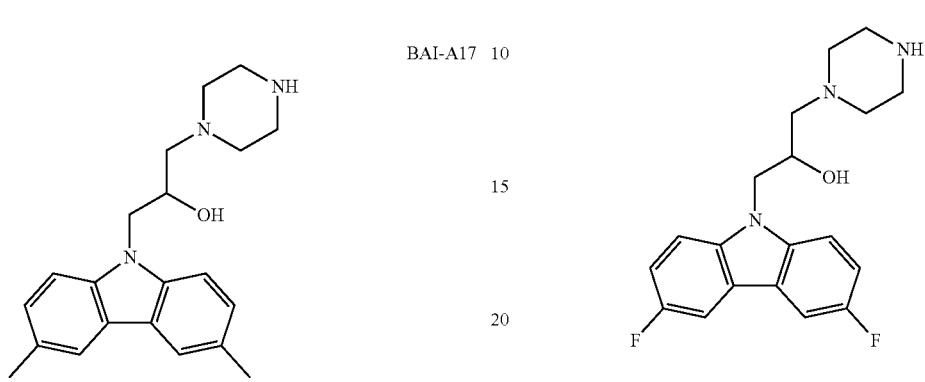

TLC: $R_f$ 0.02 (95:5, CH$_2$Cl$_2$:MeOH). ¹H-NMR (600 MHz, acetone-d$_6$): δ 7.86 (s, 2H), 7.49 (d, J=8.3 Hz, 2H), 7.23 (dd, J=8.3, 1.4 Hz, 2H), 4.48 (dd, J=14.8, 4.7 Hz, 1H), 4.35 (dd, J=14.8, 6.6 Hz, 1H), 4.30 (dddd, J=7.0, 6.6, 5.0, 4.7 Hz, 1H), 3.30-3.25 (m, 4H), 2.85-2.83 (m, 2H), 2.76 (dd, J=11.4, 6.2 Hz, 2H), 2.62 (dd, J=12.8, 5.0 Hz, 1H), 2.54 (dd, J=12.8, 7.0 Hz, 1H), 2.48 (s, 6H). ¹³C-NMR (151 MHz, acetone-d$_6$): δ 140.6, 128.4, 127.5, 123.6, 120.6, 110.3, 68.27, 62.5, 51.5, 48.3, 44.37, 21.4. ESI-MS m/z (rel int): (pos) 338.00 ([M+Na]⁺, 100).

TLC: $R_f$ 0.02 (95:5, CH$_2$Cl$_2$:MeOH). ¹H-NMR (600 MHz, acetone-d$_6$): δ 7.89 (dd, J=9.1, 2.6 Hz, 2H), 7.69 (dd, J=9.0, 4.3 Hz, 2H), 7.27 (ddd, J=9.1, 9.0, 2.6 Hz, 2H), 4.59 (dd, J=15.1, 4.0 Hz, 1H), 4.45 (dd, J=15.1, 7.0 Hz, 1H), 4.34-4.30 (m, 1H), 3.34-3.24 (m, 4H), 2.89-2.78 (m, 4H), 2.67 (dd, J=12.8, 5.5 Hz, 1H), 2.56 (dd, J=12.8, 6.9 Hz, 1H). ¹³C-NMR (151 MHz, acetone-d$_6$): δ 157.9 (d, J=233.3 Hz,), 139.5, 123.5 (dd, J=9.9, 4.3 Hz), 114.6 (d, J=25.4 Hz), 112.1 (d, J=8.9 Hz), 106.6 (d, J=24.1 Hz), 68.4, 62.4, 51.7, 48.6, 44.5. ESI-MS m/z (rel int): (pos) 346.0 ([M+H]⁺, 100).

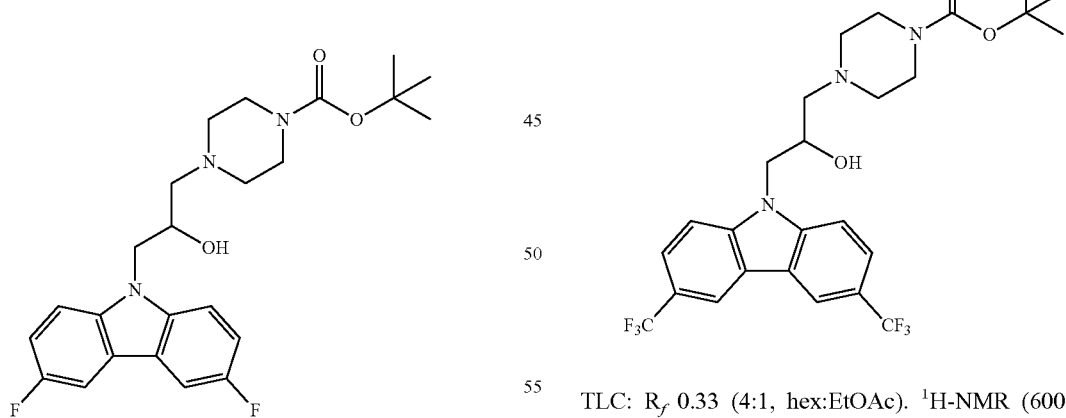

TLC: $R_f$ 0.29 (1:1, hex:EtOAc). ¹H-NMR (600 MHz, CDCl$_3$): δ 7.66 (dd, J=8.7, 2.5 Hz, 2H), 7.39 (dd, J=8.9, 4.1 Hz, 2H), 7.20 (ddd, J=8.9, 8.7, 2.5 Hz, 2H), 4.35 (dd, J=15.3, 4.5 Hz, 1H), 4.29 (dd, J=15.3, 5.7 Hz, 1H), 4.18 (ddt, J=9.1, 5.6, 4.6 Hz, 1H), 3.46-3.35 (m, 5H), 2.53 (s, 2H), 2.45-2.39 (m, 2H), 2.30 (s, 2H), 1.44 (s, 9H). ¹³C-NMR (151 MHz, CDCl$_3$): δ 157.4 (d, J=236.4 Hz), 154.8, 138.4, 123.0 (dd, J=9.5, 4.1 Hz), 114.3 (d, J=25.4 Hz), 110.2 (d, J=8.9 Hz), 106.2 (d, J=23.4 Hz), 80.0, 66.6, 61.7, 53.1, 47.5, 43.7 (d, TLC: $R_f$ 0.33 (4:1, hex:EtOAc). ¹H-NMR (600 MHz, CDCl$_3$): δ 8.39 (t, J=1.0 Hz, 2H), 7.75 (dd, J=8.6, 1.0 Hz, 2H), 7.61 (d, J=8.6 Hz, 2H), 4.47 (dd, J=15.3, 4.0 Hz, 1H), 4.38 (dd, J=15.3, 5.9 Hz, 1H), 4.21 (dddd, J=10.2, 6.0, 4.0, 3.8 Hz, 1H), 3.47 (br s, 1H), 3.50-3.36 (m, J=4.1 Hz, 4H), 2.58-2.53 (m, 2H), 2.49 (dd, J=12.3, 3.8 Hz, 1H), 2.41 (dd, J=12.3, 10.2 Hz, 1H), 2.34-2.30 (m, 2H), 1.44 (s, 9H). ¹³C-NMR (151 MHz, CDCl$_3$): δ 154.8, 143.3, 125.1 (q, J=272.0 Hz), 123.6 (q, J=3.5 Hz), 122.6 (q, J=32.5 Hz), 122.4, 118.3 (q, J=4.0 Hz), 110.1, 80.1, 66.5, 61.6, 53.1, 47.5, 43.7 (d, br), 28.5. ESI-MS m/z (rel int): (pos) 546.1 ([M+H]⁺, 100).

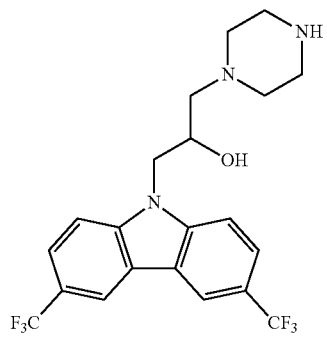 [SMILES: OC(CN1CCNCC1)Cn1c2ccc(C(F)(F)F)cc2c2cc(C(F)(F)F)ccc21]

TLC: $R_f$ 0.00 (1:1, hex:EtOAc). $^1$H-NMR (600 MHz, acetone-$d_6$): δ 8.74 (t, J=0.8 Hz, 2H), 7.98 (d, J=8.7 Hz, 2H), 7.84 (dd, J=8.7, 1.5 Hz, 2H), 4.76 (dd, J=15.1, 3.5 Hz, 1H), 4.61 (dd, J=15.1, 7.4 Hz, 1H), 4.38 (dddd, J=7.4, 6.8, 6.0, 3.5 Hz, 1H), 3.20 (t, J=5.1 Hz, 4H), 2.79-2.74 (m, 4H), 2.70 (dd, J=12.7, 6.0 Hz, 1H), 2.59 (dd, J=12.7, 6.8 Hz, 1H). $^{13}$C-NMR (151 MHz, acetone-$d_6$): δ 143.7, 125.5 (q, J=270.6 Hz), 123.0 (q, J=3.5 Hz), 122.1, 121.3 (q, J=31.9 Hz), 118.3 (q, J=4.3 Hz), 111.2, 67.4, 61.7, 52.1, 47.9, 44.3. ESI-MS m/z (rel int): (pos) 446.0 ([M+H]$^+$, 100).

TLC: $R_f$ 0.30 (1:1, hex:EtOAc). $^1$H-NMR (600 MHz, CDCl$_3$): δ (d, J=7.8 Hz, 1H), 7.30 (d, J=8.2 Hz, 1H), 7.20 (t, J=7.6 Hz, 1H), 7.10 (t, J=7.4 Hz, 1H), 6.94 (s, 1H), 4.15 (dd, J=14.7, 4.7 Hz, 1H), 4.11 (dd, J=14.7, 5.5 Hz, 1H), 4.05 (dq, J=9.5, 4.8 Hz, 1H), 3.48-3.34 (m, 4H), 2.53-2.49 (m, 2H), 2.36-2.30 (m, 7H), 1.44 (s, 9H). $^{13}$C-NMR (151 MHz, CDCl$_3$): δ 154.8, 137.0, 128.9, 126.5, 121.7, 119.2, 118.8, 110.9, 109.3, 80.0, 66.6, 61.5, 53.1, 49.7, 43.8 (d, br), 28.5, 9.8. ESI-MS m/z (rel int): (pos) 396.1 ([M+Na]+, 63), 374.0 ([M+H]$^+$, 100).

BAI-A20

TLC: $R_f$ 0.03 (95:5, CH$_2$Cl$_2$:MeOH). $^1$H-NMR (600 MHz, acetone-$d_6$): δ 7.49 (dd, J=7.8, 0.8 Hz, 1H), 7.43 (d, J=8.2 Hz, 1H), 7.12 (ddd, J=8.2, 7.1, 1.1 Hz, 1H), 7.07 (s, 1H), 7.02 (ddd, J=7.8, 7.1, 0.8 Hz, 1H), 4.68-4.64 (m, 1H), 4.32 (dd, J=14.7, 4.4 Hz, 1H), 4.23 (dd, J=14.7, 7.0 Hz, 1H), 3.98-3.86 (m, 4H), 3.81 (t, J=9.7 Hz, 4H), 3.57 (d, J=12.6 Hz, 1H), 3.39 (dd, J=12.6, 10.3 Hz, 1H), 2.26 (s, 3H), 2.05 (s, 4H). $^{13}$C-NMR (151 MHz, acetone-$d_6$): δ 137.9, 129.8, 127.5, 122.1, 122.1, 119.4 (2 carbons, confirmed by HSQC), 110.8, 110.4, 66.4, 61.1, 50.5, 50.3, 41.8, 9.6. ESI-MS m/z (rel int): (pos) 274.1 ([M+H]$^+$, 100).

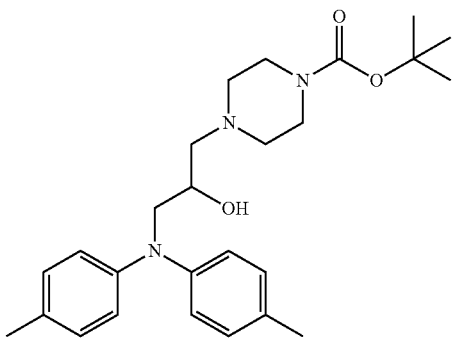 [SMILES: Cc1ccc(N(CC(O)CN2CCN(C(=O)OC(C)(C)C)CC2)c2ccc(C)cc2)cc1]

TLC: $R_f$ 0.46 (1:1, hex:EtOAc). $^1$H-NMR (600 MHz, CDCl$_3$): δ 7.05 (d, J=8.3 Hz, 4H), 6.91 (d, J=8.3 Hz, 4H), 4.01 (dtd, J=9.6, 5.9, 3.5 Hz, 1H), 3.73 (d, J=5.9 Hz, 2H), 3.43-3.36 (m, 4H), 2.54-2.48 (m, 2H), 2.45 (dd, J=12.5, 3.5 Hz, 1H), 2.37-2.30 (m, J=10.2 Hz, 3H), 2.29 (s, 6H), 1.45 (s, 9H). $^{13}$C-NMR (151 MHz, CDCl$_3$): δ 154.8, 146.4, 131.0, 130.0, 121.2, 79.9, 65.3, 62.4, 57.1, 53.3, 43.7 (d, br), 28.6, 20.8. ESI-MS m/z (rel int): (pos) 462.1 ([M+Na]$^+$, 41), 440.1 ([M+H]$^+$, 100).

BAI-A19

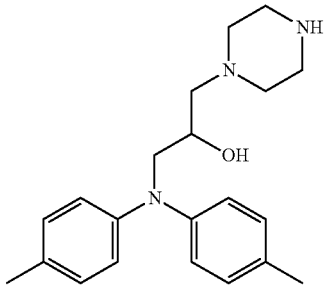

TLC: $R_f$ 0.00 (1:1, hex:EtOAc). $^1$H-NMR (600 MHz, acetone-$d_6$): δ 7.05 (d, J=8.3 Hz, 4H), 6.96 (d, J=8.3 Hz, 4H), 4.03 (dddd, J=7.5, 6.8, 4.9, 4.4 Hz, 1H), 3.91 (dd, J=14.9, 4.9 Hz, 1H), 3.62 (dd, J=14.9, 6.8 Hz, 1H), 3.20 (t, J=5.1 Hz, 4H), 2.83-2.79 (m, 2H), 2.73-2.70 (m, 2H), 2.58 (dd, J=12.8, 4.4 Hz, 1H), 2.48 (dd, J=12.8, 7.5 Hz, 1H), 2.25 (s, 6H). $^{13}$C-NMR (151 MHz, acetone-$d_6$): δ 147.4, 131.0, 130.4, 121.9, 66.9, 62.9, 57.7, 51.9, 44.6, 20.6. ESI-MS m/z (rel int): (pos) 340.0 ([M+H]$^+$, 100).

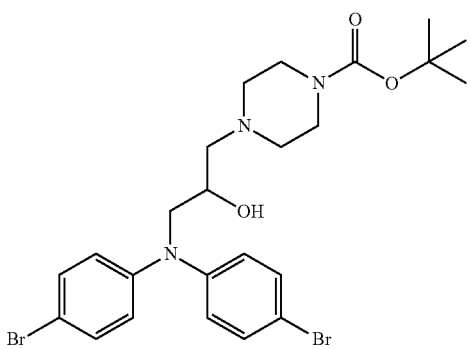 [SMILES: CC(C)(C)OC(=O)N1CCN(CC(O)CN(c2ccc(Br)cc2)c2ccc(Br)cc2)CC1]

TLC: $R_f$ 0.60 (1:1, hex:EtOAc). $^1$H-NMR (600 MHz, CDCl$_3$): δ 7.35 (d, J=7.1 Hz, 4H) 6.94 (d, J=7.1 Hz, 4H), 3.99-3.95 (m, 1H), 3.75 (dd, J=15.3, 4.1 Hz, 1H), 3.66 (dd, J=15.3, 7.1 Hz, 1H), 3.44-3.38 (m, 4H), 2.54 (m, 2H), 2.39 (dd, J=12.4, 3.7 Hz, 1H), 2.36-2.29 (m, 3H), 1.45 (s, 9H). $^{13}$C-NMR (151 MHz, CDCl$_3$): δ 154.6, 147.0, 132.3, 122.9, 114.4, 79.8, 64.7, 62.0, 56.6, 53.1, 43.6 (d, br), 28.4. ESI-MS m/z (rel int): (pos) 568.0 ([M($^{81}$Br,$^{81}$Br)+H]$^+$,50) 570.0 ([M($^{81}$Br,$^{79}$Br)+H]+, 100), 572.1 ([M($^{79}$Br,$^{79}$Br)+H]$^+$, 50).

BAI-A21

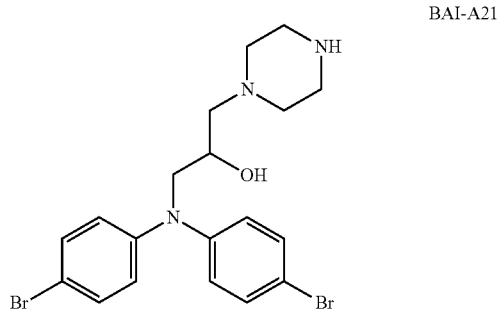 [SMILES: OC(CN1CCNCC1)CN(c1ccc(Br)cc1)c1ccc(Br)cc1]

TLC: $R_f$ 0.00 (1:1, hex:EtOAc). $^1$H-NMR (600 MHz, CD$_3$CN): δ 7.38 (d, J=8.9 Hz, 4H), 7.00 (d, J=8.9 Hz, 4H), 3.94-3.90 (m, 1H), 3.86 (dd, J=15.3, 3.7 Hz, 1H), 3.57 (dd, J=15.3, 7.7 Hz, 1H), 3.14 (q, J=5.9 Hz, 4H), 2.75-2.73 (m, 2H), 2.66-2.64 (m, 2H), 2.46 (dd, J=12.6, 4.0 Hz, 2H), 2.40 (dd, J=12.6, 8.1 Hz, 2H). $^{13}$C-NMR (151 MHz, CD$_3$CN): δ 148.3, 133.0, 124.1, 114.4, 66.5, 62.1, 57.3, 51.1, 44.4, 1.32, 1.18. ESI-MS m/z (rel int): (pos) 471.9 ([M($^{81}$Br,$^{81}$Br)+H]$^+$, 50) 469.9 ([M($^{81}$Br,$^{79}$Br)+H]$^+$, 100), 467.9 ([M($^{79}$Br,$^{79}$Br)+H]$^+$, 50).

REFERENCES

1. Whelan R S, Kaplinskiy V and Kitsis R N. Cell death in the pathogenesis of heart disease: mechanisms and significance. *Annual review of physiology.* 2010; 72:19-44.
2. Kung G, Konstantinidis K and Kitsis R N. Programmed necrosis, not apoptosis, in the heart. *Circulation research.* 2011; 108:1017-36.
3. Konstantinidis K, Whelan R S and Kitsis R N. Mechanisms of cell death in heart disease. *Arteriosclerosis, thrombosis, and vascular biology.* 2012; 32:1552-62.
4. Christia P and Frangogiannis N G. Targeting inflammatory pathways in myocardial infarction. *European Journal of Clinical Investigation.* 2013; 43:986-995.
5. Diwan A, Krenz M, Syed F M, Wansapura J, Ren X, Koesters A G, Li H, Kirshenbaum L A, Hahn H S, Robbins J, Jones W K and Ii G W D. Inhibition of ischemic cardiomyocyte apoptosis through targeted ablation of Bnip3 restrains postinfarction remodeling in mice. *The Journal of clinical investigation.* 2007; 117:2825-2833.
6. Pfeffer M A and Braunwald E. Ventricular remodeling after myocardial infarction. Experimental observations and clinical implications. *Circulation.* 1990; 81:1161-72.
7. Miller T D, Christian T F, Hopfenspirger M R, Hodge D O, Gersh B J and Gibbons R J. Infarct Size After Acute Myocardial Infarction Measured by Quantitative Tomographic 99mTc Sestamibi Imaging Predicts Subsequent Mortality. *Circulation.* 1995; 92:334-341.
8. Levy S. Secondary prevention after myocardial infarction: in favor of beta-blockers. *Journal of cardiovascular pharmacology.* 1990; 16 Suppl 6: S50-4.
9. Yusuf S, Peto R, Lewis J, Collins R and Sleight P. Beta blockade during and after myocardial infarction: an overview of the randomized trials. *Progress in cardiovascular diseases.* 1985; 27:335-71.
10. Yusuf S. Early intravenous beta blockade in acute myocardial infarction. *Postgraduate medicine.* 1988; Spec No:90-5.
11. Braunwald E. The Open-Artery Theory Is Alive and Well—Again. *New Engl J Med.* 1993; 329:1650-1652.
12. Feit F, Mueller H S, Braunwald E, Ross R, Hodges M, Herman M V and Knatterud G L. Thrombolysis in Myocardial Infarction (TIMI) phase II trial: Outcome comparison of a "conservative strategy" in community versus tertiary hospitals. *Journal of the American College of Cardiology.* 1990; 16:1529-1534.
13. Chi L G, Tamura Y, Hoff P T, Macha M, Gallagher K P, Schork M A and Lucchesi B R. Effect of superoxide dismutase on myocardial infarct size in the canine heart after 6 hours of regional ischemia and reperfusion: a demonstration of myocardial salvage. *Circulation research.* 1989; 64:665-75.
14. Rupprecht H J, vom Dahl J, Terres W, Seyfarth K M, Richardt G, Schultheibeta H P, Buerke M, Sheehan F H and Drexler H. Cardioprotective effects of the Na(+)/H(+) exchange inhibitor cariporide in patients with acute anterior myocardial infarction undergoing direct PTCA. *Circulation.* 2000; 101:2902-8.
15. Arai M, Lefer D J, So T, DiPaula A, Aversano T and Becker L C. An anti-CD18 antibody limits infarct size and preserves left ventricular function in dogs with ischemia and 48-hour reperfusion. *J Am Coll Cardiol.* 1996; 27:1278-85.
16. Williams F M, Kus M, Tanda K and Williams T J. Effect of duration of ischaemia on reduction of myocardial infarct size by inhibition of neutrophil accumulation using an anti-CD18 monoclonal antibody. *British Journal of Pharmacology.* 1994; 111:1123-1128.
17. Whelan R S, Konstantinidis K, Wei A C, Chen Y, Reyna D E, Jha S, Yang Y, Calvert J W, Lindsten T, Thompson C B, Crow M T, Gavathiotis E, Dorn G W, 2nd, O'Rourke B and Kitsis R N. Bax regulates primary necrosis through mitochondrial dynamics. *Proceedings of the National Academy of Sciences of the United States of America.* 2012; 109:6566-71.
18. Hochhauser E, Kivity S, Offen D, Maulik N, Otani H, Barhum Y, Pannet H, Shneyvays V, Shainberg A, Goldshtaub V, Tobar A and Vidne B A. Bax ablation protects against myocardial ischemia-reperfusion injury in transgenic mice. *American journal of physiology Heart and circulatory physiology.* 2003; 284:H2351-9.

19. Peixoto P M, Ryu S Y, Bombrun A, Antonsson B and Kinnally K W. MAC inhibitors suppress mitochondrial apoptosis. *The Biochemical journal.* 2009; 423:381-7.
20. Bombrun A, Gerber P, Casi G, Terradillos O, Antonsson B and Halazy S. 3,6-dibromocarbazole piperazine derivatives of 2-propanol as first inhibitors of cytochrome c release via Bax channel modulation. *Journal of medicinal chemistry.* 2003; 46:4365-8.
21. Gavathiotis E, Reyna D E, Bellairs J A, Leshchiner E S and Walensky L D. Direct and selective small-molecule activation of proapoptotic BAX. *Nature chemical biology.* 2012; 8:639-45.
22. Bedford, R. B.; Betham, M.; Charmant, J. P. H.; Weeks, A. L.; Tetrahedron 2008, 64, 6038-6050.
23. McKnight, Steven L.; Pieper, Andrew A.; Ready, Joseph M.; De Brabander, Jef K.; U.S. Pat. Appl. Publ. 2012, US 20120022096 A1; Jan. 26, 2012.
24. Mudadu, M. S.; Singh, A. N.; Thummel, R. P.; J. Org. Chem 2008, 73, 6513-6520.
25. Bombrun, A.; Gerber, P.; Casi, G.; Terradillos, O.; Antonsson, B.; Halazy, S.; J. Med. Chem, 2003, 46, 4365-4368.
26. Sapountzis, I.; Knochel, P.; J. Am. Chem. Soc. 2002, 124, 9390-9391.
27. Ky, B., Vejpongsa, P., Yeh, E. T., Force, T., and Moslehi, J. J. (2013). Emerging paradigms in cardiomyopathies associated with cancer therapies. Circulation Research, 113(6):754-764.
28. Carvalho, C., Santos, R. X., Cardoso, S., Correia, S., Oliveira, P. J., Santos, M. S., and Moreira, P. I. (2009). Doxorubicin: the good, the bad and the ugly effect. Current medicinal chemistry, 16(25):3267-3285.
29. Cardinale, D., Colombo, A., Bacchiani, G., Tedeschi, I., Meroni, C. A., Veglia, F., Civelli, M., Lamantia, G., Colombo, N., Curigliano, G., et al. (2015). Early detection of anthracycline cardiotoxicity and improvement with heart failure therapy. Circulation, pages CIRCULATIONAHA-114.
30. Delgado, R. M., Nawar, M. A., Zewail, A. M., Kar, B., Vaughn, W. K., Wu, K. K., Aleksic, N., Sivasubramanian, N., McKay, K., Mann, D. L., et al. (2004). Cyclooxygenase-2 inhibitor treatment improves left ventricular function and mortality in a murine model of doxorubicin-induced heart failure. Circulation, 109(11):1428-1433.
31. Liu, X.-J., Wang, X.-G., Zhang, X., Xie, Y.-Q., Chen, R.-Z., and Chen, H.-Z. (2012). C57bl/6 mice are more appropriate than balb/c mice in inducing dilated cardiomyopathy with short-term doxorubicin treatment. Acta Cardiologica Sinica, 28(3):236-240.
32. Milano, G., Raucci, A., Scopece, A., Daniele, R., Guerrini, U., Sironi, L., Cardinale, D., Capogrossi, M. C., and Pompilio, G. (2014). Doxorubicin and trastuzumab regimen induces biventricular failure in mice. Journal of the American Society of Echocardiography, 27(5):568-579.
33. Ky, B., Vejpongsa, P., Yeh, E. T., Force, T., and Moslehi, J. J. (2013). Emerging paradigms in cardiomyopathies associated with cancer therapies. Circulation Research, 113(6):754-764.
34. Moja, L., Tagliabue, L., Balduzzi, S., Parmelli, E., Pistotti, V., Guarneri, V., and D'amico, R. (2006). Trastuzumab containing regimens for early breast cancer. Cochrane Database Syst Rev, 4.
35. Slamon, D. J., Leyland-Jones, B., Shak, S., Fuchs, H., Paton, V., Bajamonde, A., Fleming, T., Eiermann, W., Wolter, J., Pegram, M., et al. (2001). Use of chemotherapy plus a monoclonal antibody against her2 for metastatic breast cancer that overexpresses her2. New England Journal of Medicine, 344(11):783-792.

What is claimed is:

1. A compound having the structure of formula (VII)

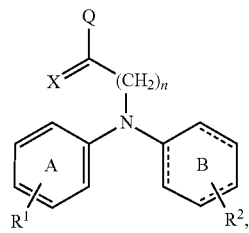

(VII)

wherein

A is phenyl;

B is phenyl;

R1 and R2 are independently none, C1-C5 alkyl, F, Cl, Br, I, CN, $NO_2$, $NR4_2$, OR4, $CF_3$, COOH, COOR4, NHR4, OCR4, SR4, SOR4, or $SO_2R4$;

X is F, Cl, Br, I, $NR4_2$, or OR4; wherein the bond between X and the main scaffold is a single bond;

Q is

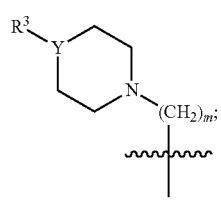

R3 is none, H, C1-C6 alkyl, R4(C=O), or $(CH_2)_pOH$;

R4 is H or C1-C3 alkyl;

Y is S, or N;

p is 1-3;

m is 1 and n is 1;

or a pharmaceutically acceptable salt thereof.

2. The compound or a pharmaceutically acceptable salt thereof of claim 1, wherein the compound is selected from the group consisting of

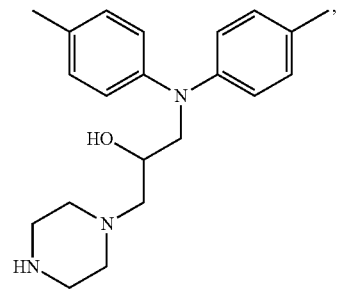

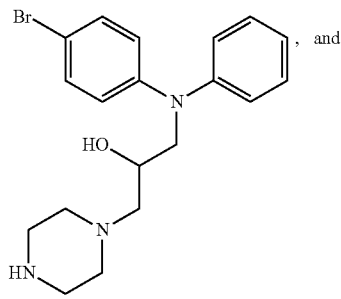

, and

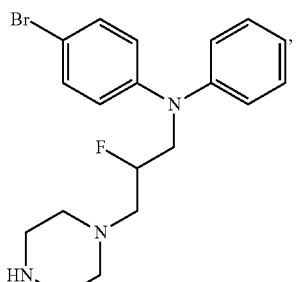

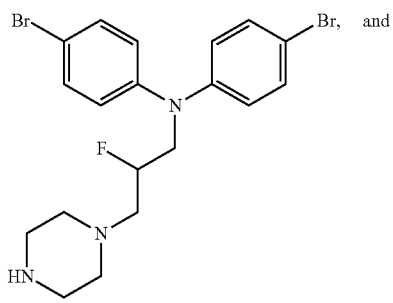

, and

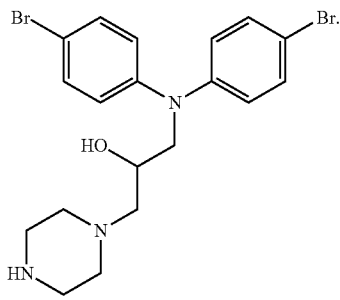

3. The compound or a pharmaceutically acceptable salt thereof of claim 1, where R1 and/or R2 are in the para position with respect to the bond to the N atom.

4. A pharmaceutical composition comprising one or more of the compounds of claim 1, and a pharmaceutically acceptable carrier.

5. The compound or a pharmaceutically acceptable salt thereof of claim 1, wherein X is OH or F.

6. The compound or a pharmaceutically acceptable salt thereof of claim 1, wherein R3 is none, H, C1-C6 alkyl, or $(CH_2)_p OH$.

7. The compound or a pharmaceutically acceptable salt thereof of claim 1, wherein R3 is none or H.

8. The compound or a pharmaceutically acceptable salt thereof of claim 1, wherein X is OH or F.

9. The compound or a pharmaceutically acceptable salt thereof of claim 1, wherein:

R1 and R2 are independently none, C1-C5 alkyl, F, Cl, Br, I, OR4, $CF_3$, or CN;

R3 is none, H, C1-C6 alkyl, or $(CH_2)_p OH$;

X is F or OH; and

Y is N.

10. The compound or a pharmaceutically acceptable salt thereof of claim 9, wherein R1 is none and R2 is C1-C5 alkyl, F, Cl, Br, $CF_3$ or I.

11. The compound or a pharmaceutically acceptable salt thereof of claim 10, wherein R2 is F, Cl, Br, or $CF_3$.

12. The compound or a pharmaceutically acceptable salt thereof of claim 2, wherein the compound is

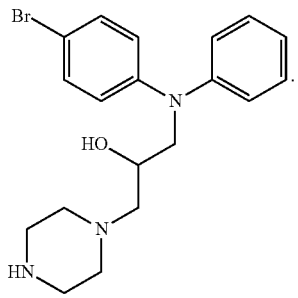 [SMILES: OC(CN1CCNCC1)CN(c1ccccc1)c1ccc(Br)cc1]

13. The compound or a pharmaceutically acceptable salt thereof of claim 2, wherein the compound is

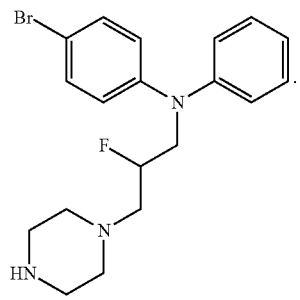 [SMILES: FC(CN1CCNCC1)CN(c1ccccc1)c1ccc(Br)cc1]

14. The compound or a pharmaceutically acceptable salt thereof of claim 2, wherein the compound is

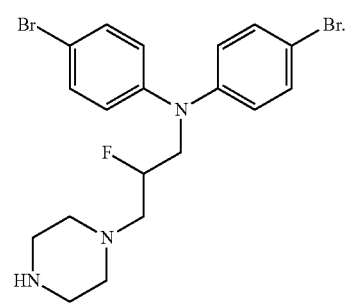 [SMILES: FC(CN1CCNCC1)CN(c1ccc(Br)cc1)c1ccc(Br)cc1]

15. The compound or a pharmaceutically acceptable salt thereof of claim 2, wherein the compound is

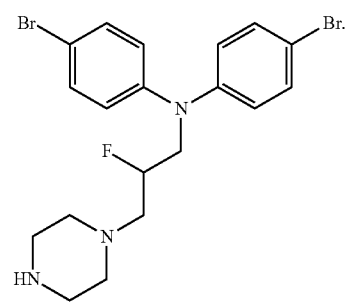 [SMILES: FC(CN1CCNCC1)CN(c1ccc(Br)cc1)c1ccc(Br)cc1]

16. The pharmaceutical composition of claim 4, wherein

R1 and R2 are independently none, C1-C5 alkyl, F, Cl, Br, I, OR4, $CF_3$, or CN;

R3 is none, H, C1-C6 alkyl, or $(CH_2)_p OH$;

X is F or OH; and

Y is N.

17. The pharmaceutical composition of claim 16, wherein R1 is none and R2 is C1-C5 alkyl, F, Cl, Br, $CF_3$ or I.

18. The pharmaceutical composition of claim 17, wherein R2 is F, Cl, Br, or $CF_3$.

19. The pharmaceutical composition of claim 4, wherein the compound is

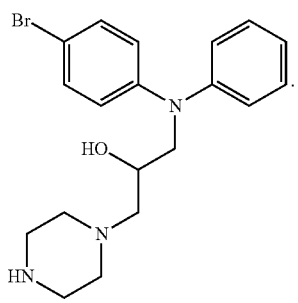 [SMILES: OC(CN1CCNCC1)CN(c1ccccc1)c1ccc(Br)cc1]
20. The pharmaceutical composition of claim 4, wherein the compound is
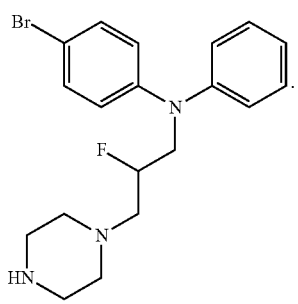 [SMILES: FC(CN1CCNCC1)CN(c1ccccc1)c1ccc(Br)cc1]
21. The pharmaceutical composition of claim 4, wherein the compound is
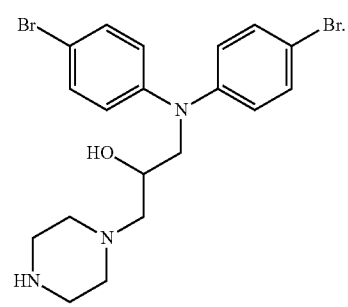 [SMILES: OC(CN1CCNCC1)CN(c1ccc(Br)cc1)c1ccc(Br)cc1]
22. The pharmaceutical composition of claim 4, wherein the compound is
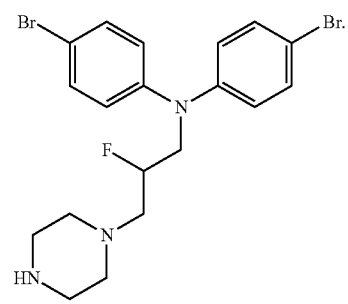 [SMILES: FC(CN1CCNCC1)CN(c1ccc(Br)cc1)c1ccc(Br)cc1]
* * * * *

SEQUENCE LISTING

<160> NUMBER OF SEQ ID NOS: 1

<210> SEQ ID NO 1
<211> LENGTH: 192
<212> TYPE: PRT
<213> ORGANISM: Homo sapiens

<400> SEQUENCE: 1

Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

```
Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Val Thr Ile Phe
                165             170             175

Val Ala Gly Val Leu Thr Ala Ser Leu Thr Ile Trp Lys Lys Met Gly
            180             185             190
```